(12) United States Patent
Yu et al.

(10) Patent No.: US 9,238,813 B2
(45) Date of Patent: Jan. 19, 2016

(54) TARGETED PRE-MRNA/MRNA MODIFICATION AND GENE REGULATION

(71) Applicants: Yi-Tao Yu, Pittsford, NY (US); Xinliang Zhao, Rochester, NY (US)

(72) Inventors: Yi-Tao Yu, Pittsford, NY (US); Xinliang Zhao, Rochester, NY (US)

(73) Assignee: University of Rochester, Rochester, NY (US)

( * ) Notice: Subject to any disclaimer, the term of this patent is extended or adjusted under 35 U.S.C. 154(b) by 0 days.

(21) Appl. No.: 14/056,309

(22) Filed: Oct. 17, 2013

(65) Prior Publication Data

US 2014/0186300 A1  Jul. 3, 2014

Related U.S. Application Data

(62) Division of application No. 11/606,995, filed on Dec. 1, 2006, now Pat. No. 8,603,457.

(60) Provisional application No. 60/741,543, filed on Dec. 2, 2005.

(51) Int. Cl.
  C07H 21/04 (2006.01)
  C12N 15/113 (2010.01)
  C12N 15/63 (2006.01)
  A61K 48/00 (2006.01)

(52) U.S. Cl.
  CPC .............. *C12N 15/113* (2013.01); *C12N 15/63* (2013.01); *A61K 48/00* (2013.01)

(58) Field of Classification Search
  None
  See application file for complete search history.

(56) References Cited

U.S. PATENT DOCUMENTS 5,972,705 A * 10/1999 Fournier et al. ............... 435/440

* cited by examiner

*Primary Examiner* — Kimberly Chong
(74) *Attorney, Agent, or Firm* — Sterne, Kessler, Goldstein & Fox P.L.L.C.

(57) ABSTRACT

Methods for affecting mRNA expression or translation through the modification of pre-mRNA or mRNA transcripts are described. In one embodiment of the methods of the present invention, the branch point adenosine of a pre-mRNA transcript is 2'-0-methylated to block splicing and subsequent expression of the protein encoded by the transcript. In another embodiment, a uridine residue in a nonsense stop codon may be modified to pseudouridine, causing the translation machinery to read through the nonsense stop codon and translate a full length protein.

19 Claims, 15 Drawing Sheets

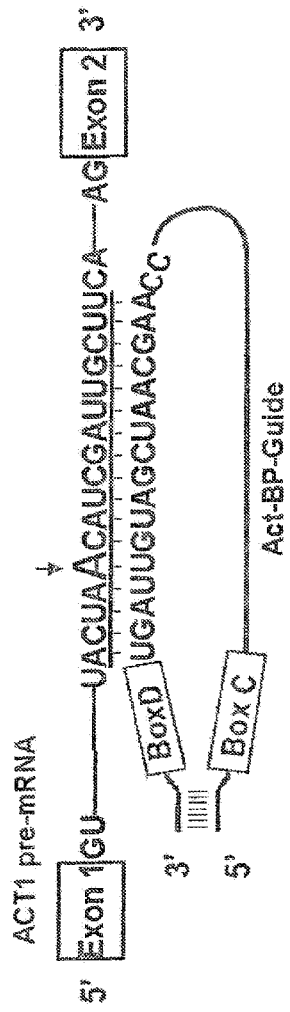
Figure 6A (SEQ ID NO. 4)
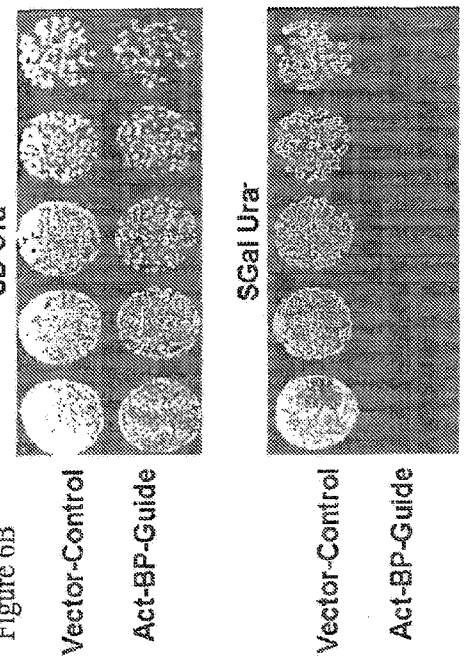
Figure 6B

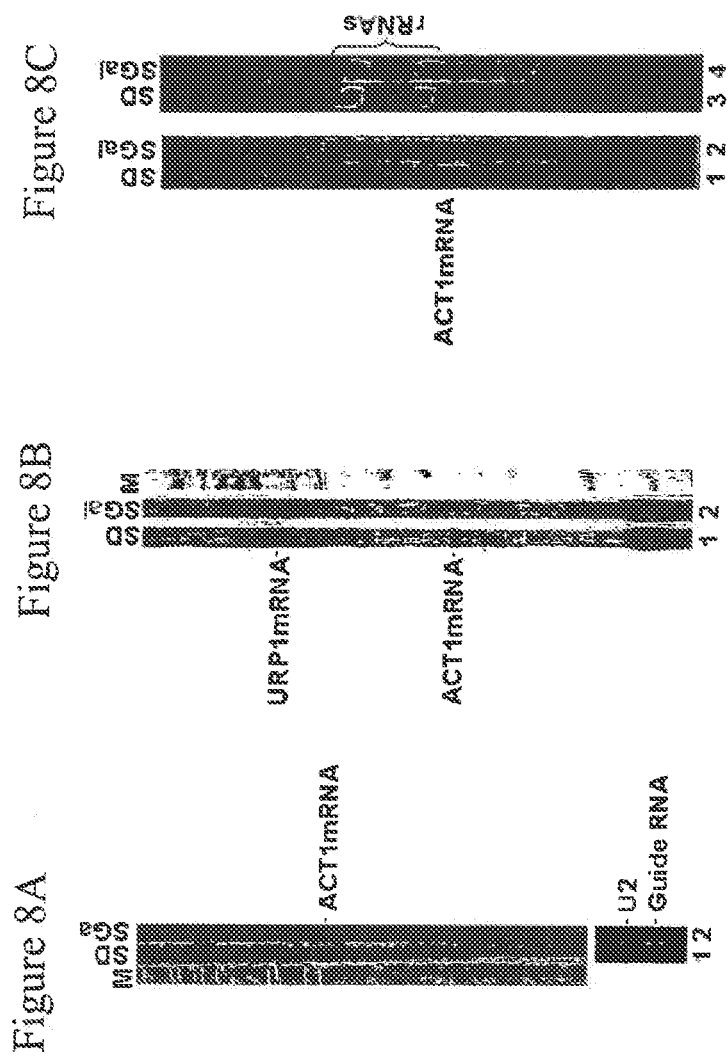

(SEQ ID NO. 4)
(SEQ ID NO. 4)

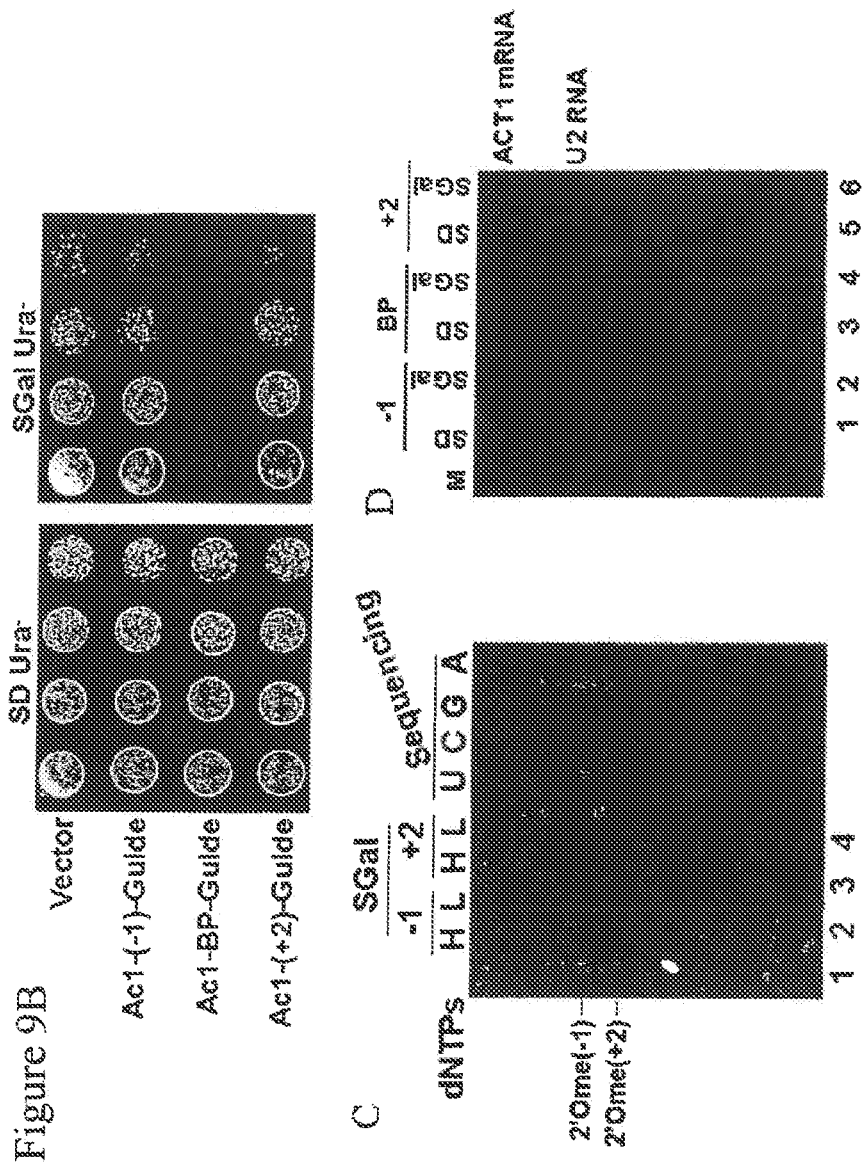

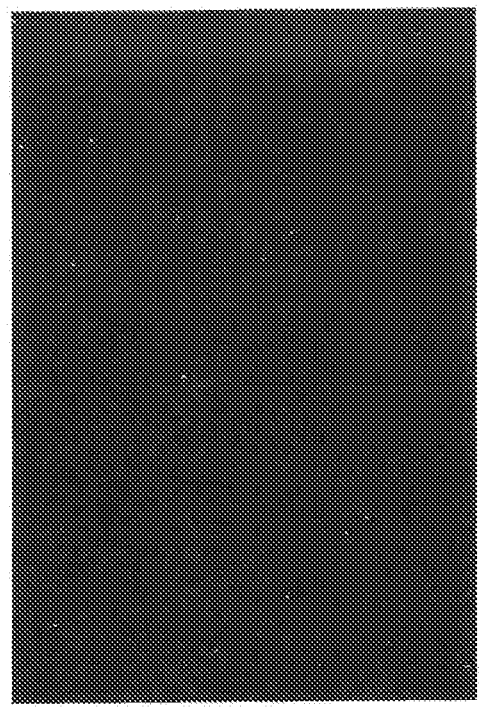
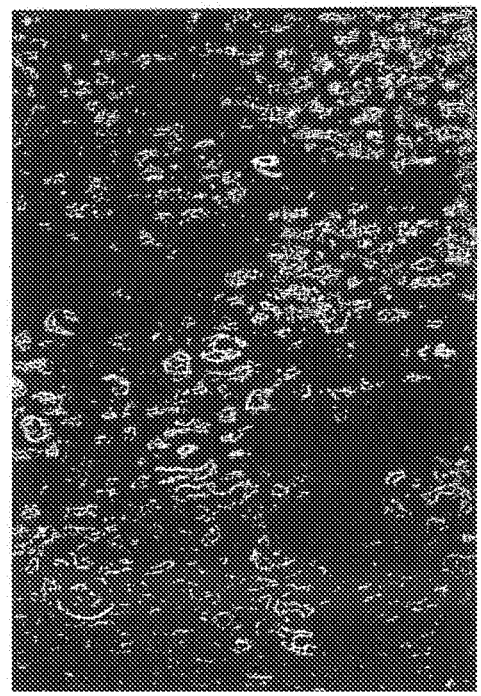
Figure 11

Figure 13

```
oligo1
------------------------------------->
T7---(Kozac sequence)---(His-Tag)----(Myc-Tag)----TAA----(Flag-Tag)--TGA
                                   <------------------------------------oligo 2
```

TARGETED PRE-MRNA/MRNA MODIFICATION AND GENE REGULATION

STATEMENT OF PRIORITY

This application claims priority to U.S. Provisional Patent Application Ser. No. 60/741,543, filed Dec. 2, 2005 whose disclosure is hereby incorporated by reference herein.

GOVERNMENT INTEREST

The subject matter of this application was made with support from the United States Government under Grant No. GM62937 from the National Institutes of Health. The United States Government may retain certain rights.

FIELD OF THE INVENTION

The present invention relates to a method for silencing genes or for manipulating alternate splicing pathways or protein translation by use of RNA modification.

BACKGROUND OF THE INVENTION

Post-transcriptional gene silencing and modification techniques have shown great promise for the treatment of disease. Gene silencing techniques are designed to repress the expression of a gene by interfering with the processing of its mRNA transcript, while modification techniques offer the possibility to correct errors in the transcript.

Currently, the main techniques for post-transcriptional gene silencing are the use of antisense oligodeoxyribonucleic acids (ODNs) and RNA interference (RNAi). Both of these methods have been developed for use both in cell culture experiments and as therapeutics.

Antisense ODNs act by hybridizing to pre-mRNAs and mRNAs to form a substrate for ribonuclease H (RNase H). RNase H then acts to cleave the ODN-RNA duplex, destroying the RNA target and preventing its expression. ODNs that are resistant to the action of RNase H can also be used to sterically inhibit splicing of a pre-mRNA. For example, an ODN can be designed to hybridize across the exon-intron junction of a pre-mRNA, preventing that pre-mRNA from being spliced and expressed.

ODNs have shown limited success in gene silencing, and their use has several disadvantages. These disadvantages stem primarily from the fact that high concentrations of ODNs must be used to elicit effective gene silencing. Use of high concentrations of ODNs, especially those of more than 20 nucleotides in length, can trigger an immune response and the production of interferons. ODNs can also bind endogenous proteins, causing unintended toxic side effects. Further, because they are synthetic oligonucleotides, ODNs may only be delivered by exogenous means, such as injection, limiting their use as a long term therapeutic.

RNAi is able to successfully cause gene silencing at concentrations at least 100 times less than those necessary for successful silencing with ODNs. In RNAi, double stranded RNA molecules or microRNA hairpins are cleaved into 21-28 fragments, which are assembled into a RNA induced silencing complex (RISC). The RISC then causes the degradation of mRNAs that contain sequence complementary to the 21-28 nucleotide fragment. Further, RNAi effector molecules are able to be transcribed from DNA, allowing for delivery of the effector molecules by a variety of methods, such as through use of viral vectors.

Because of the above advantages, RNAi has become the primary method of post-transcription gene silencing. However, the technique has several disadvantages. The first of these disadvantages is that RNAi can only be used for targeting exons, making it ineffective against pre-mRNA transcripts. This is especially important for cell culture studies where it is desirable to transfect cells with a vector encoding an exogenous version of the protein whose expression has been knocked down. As RNAi targets only exons, it will also target this exogenous transcript.

Another disadvantage of RNAi is that certain mRNA targets are refractory to its use. Because of the nature of RNAi, it is not possible to improve targeting, meaning that some genes are simply not able to be silenced with RNAi. This has complicated its use as a therapeutic. Thus far, researchers have not had widespread success in using RNAi for silencing genes in mammals in vivo.

Because of the defects in the gene silencing techniques known in the art, it is desirable to develop improved methods of post-transcriptional gene silencing. Such methods could be used as substitutes for the above techniques. Further, new methods of gene silencing could be used in combination with known techniques, especially in cell culture experiments.

U.S. Pat. No. 5,972,705 to Fournier et al., which is hereby incorporated by reference herein, discloses a method of using small nucleolar (sno) RNAs to cause the 2'-O-methylation of specific nucleotides in an mRNA. Fournier teaches use of 2'-O-methyl (2'-OMe) modifications at the 5' or 3' splice sites of pre-mRNA to prevent the cleavage of the pre-mRNA that occurs during the splicing process. In certain circumstances, blocking cleavage at the 5' or 3' splice site may prevent pro-mRNA splicing and subsequent expression. However, as the 2'-hydroxyl group of the nucleotide at either the 5' or 3' splice sites is not involved in the splicing process, it is not clear that modification at either of these sites will block splicing at all.

Although Fournier presents method of pre-mRNA modification for post-transcriptional gene silencing, the method as described has a disadvantage in that it is unable to prevent the splicing and subsequent expression of many alternatively spliced transcripts. As alternatively spliced pre-mRNAs have more than one 5' or 3' splice site, blocking the cleavage of one site will only allow the transcript to splice with another splice site, still leading to expression of the gene. Further, there are a significant number of exons that contain alternative 5' or 3' splice sites just up or down stream from the main splice site (Ast, Nature Rev. Genet. 5:773, 2004). Hence, blocking a main splice site would only lead to the use of the alternative site, and would not prevent expression of the transcript. The inability to block gene expression of certain alternatively spliced transcripts is especially significant disadvantage for human therapeutic applications, as 50% of human transcripts are estimated to be alternatively spliced.

Post transcriptional mRNA modification also has the potential to correct errors in pre-mRNA or mRNA transcripts. Modification of an mRNA transcript may cause a mutated codon to be read differently, allowing for the correction of a mutation on an mRNA level. Correction on the mRNA level may be desirable over correction at the DNA level, as genetic therapy techniques have been used with limited success and at excessive cost. Further, there is likely to be less risk of unintended consequences (such as causing a mutation elsewhere) involved in modification of the temporal mRNA transcript as compared to modification of a DNA encoded gene.

Nonsense mutations are one of the main types of mutations that may lend themselves to correction on the mRNA transcript level. A nonsense mutation is a mutation that creates an early stop codon in the coding sequence. As an early stop codon (or nonsense codon) is created, the translation machinery stops before the entire coding sequence is read, and a truncated version of the protein being encoded is formed. The truncated forms of these proteins may lead to disease pathologies such a Cystic Fibrosis and Duchene Muscular Dystrophy, among other diseases.

US Published Patent Application No. 2006/0035943 to Karp, which is hereby incorporated herein, describes use of a chemical compound to cause the translation process to bypass nonsense codons. While this method may cause the translation machinery to bypass the desired nonsense codon, it can also cause other, legitimate stop codons to be bypassed, potentially leading to undesired consequences.

Overall, there is a need in the art for methods for modifying both pre-mRNA and mRNA transcripts to prevent or modify the expression of the protein coded in those transcripts. As these methods would provide for specific targeting of sites on mRNAs, they would overcome many of the drawbacks and risks of RNA interference and gene therapy techniques.

SUMMARY OF THE INVENTION

It is an object of the present invention to provide a plasmid and method to facilitate the identification of the branch point of a mRNA transcript. A plasmid of the present invention is a chimeric adenovirus plasmid containing two exons and an intervening intron from adenovirus. The plasmid allows for nucleic acid sequence containing the branch point of interest to be inserted into the plasmid, replacing the final ⅓ of the adenovirus intron. This plasmid will allow for extensive production of chimeric mRNA transcript from which a sufficient amount of lariat-structured RNA can be isolated. Analysis of this lariat-structured RNA will then allow for the determination of the branch point of interest. Once the branch point is identified, it can be modified to prevent splicing of the pre-mRNA transcript and its subsequent expression.

It is a further object of the present invention to provide a novel method for post-transcriptional gene silencing by selectively modifying residues necessary for the splicing of pre-mRNA. Modification, such as 2'-O-methylation, of the proper residues in a pre-mRNA transcript can prevent splicing and subsequent translation of the transcript. This modification may be made through an RNA directed RNA modification process.

It is a further object of the present invention to provide a novel method for post-transcriptional gene silencing by modifying the branch point adenosine of a pre-mRNA transcript. As the branch point attacks the 5' exon/intron junction to initiate the splicing reaction, proper modification of the branch point adenosine will prevent the initiation of the splicing reaction, preventing transcript maturation and subsequent expression.

It is a further object of the present invention to provide a novel method for silencing a specific alternatively spliced variant of an mRNA transcript by specifically targeting that variant. RNA modifications can be made to block splicing in an intron that is typically excised in an alternatively spliced variant, allowing only the other variants to be produced.

It is a still further object of the present invention to provide a novel method for modifying a pre-mRNA or mRNA transcript so that a codon is read differently than its sequence, allowing for the substitution of amino acids at specific points in the final protein product. This method may be used to allow nonsense stop codons to be read as coding codons, causing the formation of a full length protein. It may also be used for other types of amino acid substitutions.

BRIEF DESCRIPTION OF THE DRAWINGS

FIG. 6A shows a schematic of the Design of an artificial guide RNA (Act-BP-Guide) targeting ACT1 pre-mRNA (SEQ ID NO. 4) for 2'-O-methylation. Act-BP-Guide was derived from S. cerevisiae snR50, a natural C/D snoRNA that guides the 2'-O-methylation of 25S rRNA at position 865. To convert snR50 into Act-BP-Guide, only the original guide sequence was changed such that the new guide sequence could base pair with the branch site of ACT1 pre-mRNA, precisely positioning the branch point adenosine 5 nucleotides upstream of the D box. Exon 1 and Exon 2 of ACT1 pre-mRNA and box C, box D and the terminal stem of Act-BP-Guide are schematically indicated. The arrow indicates the branch point adenosine. The 5' and 3' splice sites and the branch site of ACT1 pre-mRNA and the guide sequence of Act-BP-Guide are shown.

FIG. 6B shows solid media plates demonstrating the growth defect phenotype conferred by Act-BP-Guide. Vector AVA0040 (URA+), or AVA0040-derived plasmid (URA+) containing Act-BPGuide, expression of which is under control of the Gal promoter, was transformed into wild type S. cerevisiae. After streaking twice on SD medium (Ura−), a single colony was randomly selected and plated on SD or SGal medium (Ura−), as indicated. Cells expressing Act-BP-Guide exhibited a growth defect phenotype (panel SGal Ura−).

Figure 1:
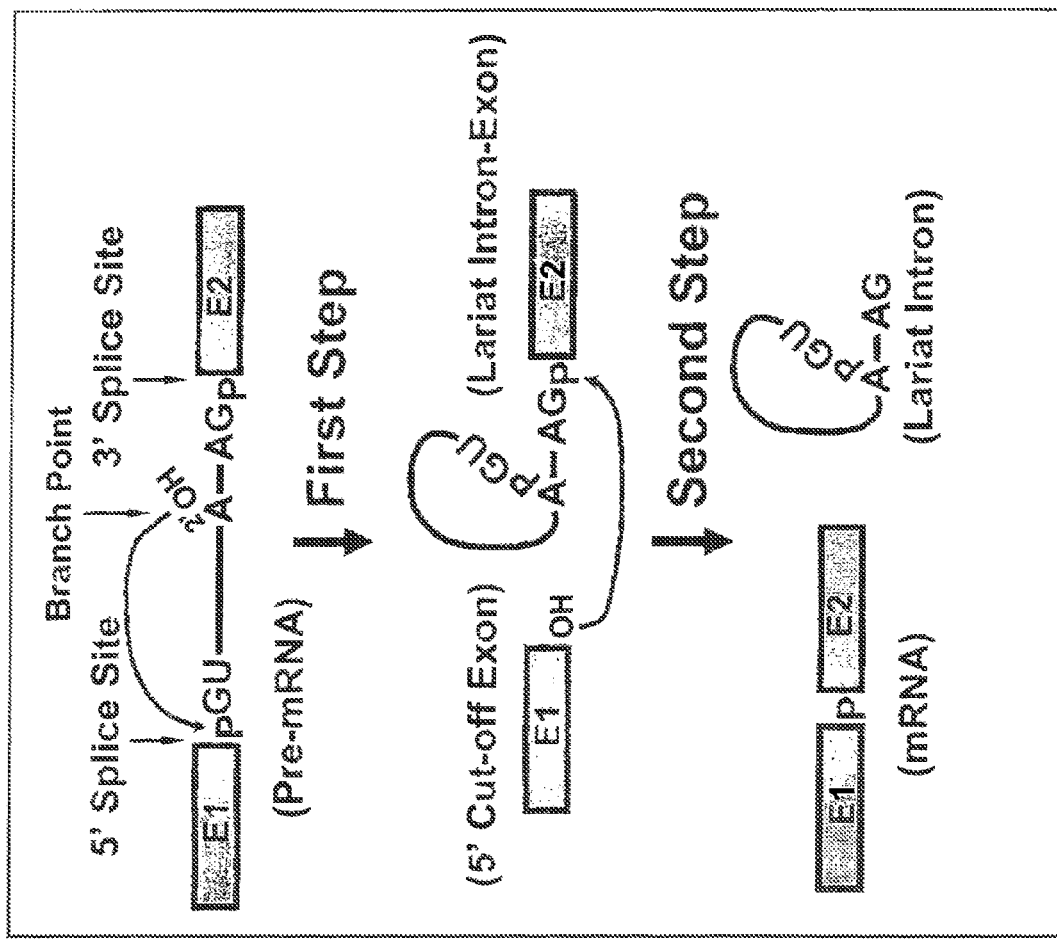
FIG. 1 shows a schematic representation of the pre-mRNA splicing pathway.

concentrations of dNTPs. Cells used in lanes 5 and 6 were grown in SD, and cells used in lanes 7 and 8 were grown in SGal for 16 h after switching from SD. A primer-extension sequencing ladder of ACT1 pre-mRNA was analyzed in parallel (lanes 1-4). The branch site sequence (UACUAA*C, where the asterisk indicates the branch point adenosine) is shown. The arrow points to the primer-extension stop (lane 8), indicating that the branch point adenosine, which is 5' adjacent to the stop site, was 2'-O-methylated.

FIG. 8A shows a primer-extension analysis. Three primers, specific for ACT mRNA, U2 or Act-BPGuide, were used in each reaction. Lane 1 is the total RNA isolated from cells grown in SD. In lane 2, total RNA was isolated from cells grown in SGal for 16 h after switching from SD. The primer-extension products of ACT mRNA, U2 and Act-BP-Guide are indicated. Lane M is a size marker of MspI-digested pBR322.

FIG. 8B shows an RNase protection analysis. Two probes, anti-ACT1 mRNA and anti-URP1 mRNA, were used. The protected ACT1 mRNA and URP1 mRNA signals are indicated. RNA and cells used in lanes 1 and 2 were identical to that in lanes 1 and 2, respectively, of panel (A).

FIG. 8C shows Northern and ethidium bromide staining analyses. Anti-ACT1 mRNA probe was used for northern analysis (lanes 1 and 2). ACT1 mRNA is indicated. The same membrane (lanes 1 and 2) was then stained with ethidium bromide (lanes 3 and 4). 18S and 25S rRNAs are indicated. RNAs and cells used in lanes 1 and 2 (and lanes 3 and 4) were identical to that in lanes 1 and 2, respectively, of panel (A).

Figure 9A:
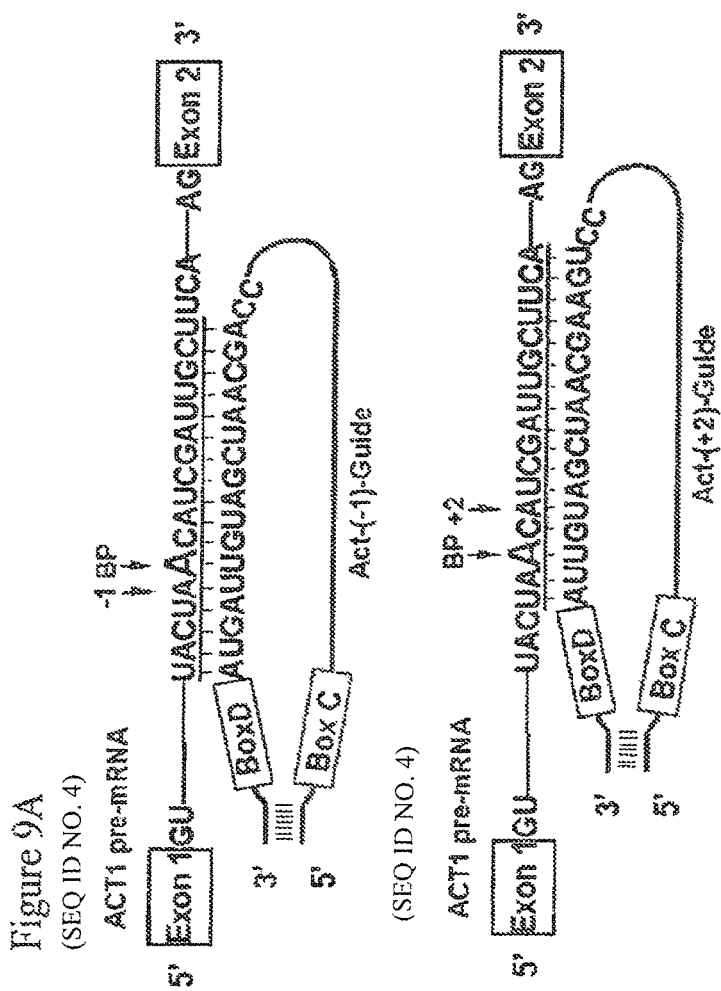

FIG. 9A shows a schematic of how the engineered guide RNA target 2'-O-methylation. Two control guide RNAs, Act-(−1)-Guide and Act-(+2)-Guide, were constructed to target the adenosine 5' adjacent (−1) to the branch point adenosine and the adenosine 2 nucleotide downstream (+2) of the branch point adenosine, respectively. The target adenosines (−1 and +2) along with the branch point adenosine (BP) are indicated. Except for the guide sequences, the guide RNA sequence and the plasmid are identical to those described in FIG. 3.

FIG. 9B shows the growth of yeast cells harboring the guide RNA plasmids. Cells transformed with the vector or with the plasmid containing one of the guide RNA sequences (indicated) were plated, in serial 2-fold dilutions, on SD or SGal medium. Although Act-BP-Guide had a strong effect on cell growth on SGal medium, Act-(−1)-Guide and Act-(+2)-Guide had no effect on cell growth. (C) Site-specific 2'-O-methylation in ACT1 pro-mRNA was identified in SGal-cultured cells that had been transformed with the plasmid containing either Act-(−1)-Guide (lanes 1 and 2) or Act-(+2)-Guide (lanes 3 and 4). Modification signals at −1 and +2 positions are indicated. The assay was identical to that described in the FIG. 7B legend.

FIG. 9D shows a primer extension analysis. ACT1 mRNA levels were analyzed by primer-extension analysis (refer to legend to FIG. 5A for details). Although ACT1 mRNA was nearly completely abolished when Act-BP-Guide was expressed (lane 4), the expression of Act-(−1)-Guide (lane 2) or Act-(+2)-Guide (lane 6) had no effect on ACT1 mRNA level.

Figure 10:
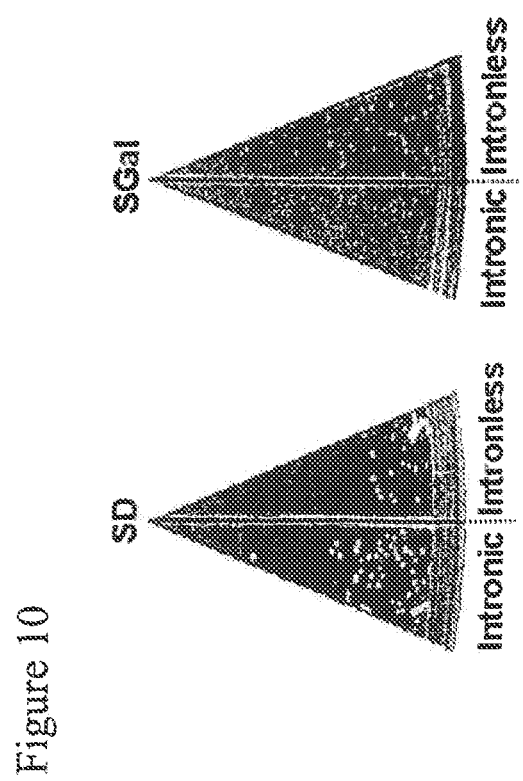

FIG. 10 shows the ACT1 mRNA-mediated rescue of cell growth. Act-BP-Guide-transformed cells were transformed with a plasmid containing either a mature ACT1 gene (Intron-less) or a pre-ACT1 gone (Intronic), expression of which was under control of the Gal promoter. After transformation, cells were streaked onto SD or SGal medium. Although the yeast strains transformed with the plasmid containing either intronic or intron-less ACT1 gene grew on both media (the left panel), only the strain that had been transformed with the plasmid containing intron-less ACT1 gene grew on SGal (the right panel).

FIG. 11 shows a phase image and fluorescent image of yeast cells taking up engineered RNA as described in Example 5.

Figure 12:
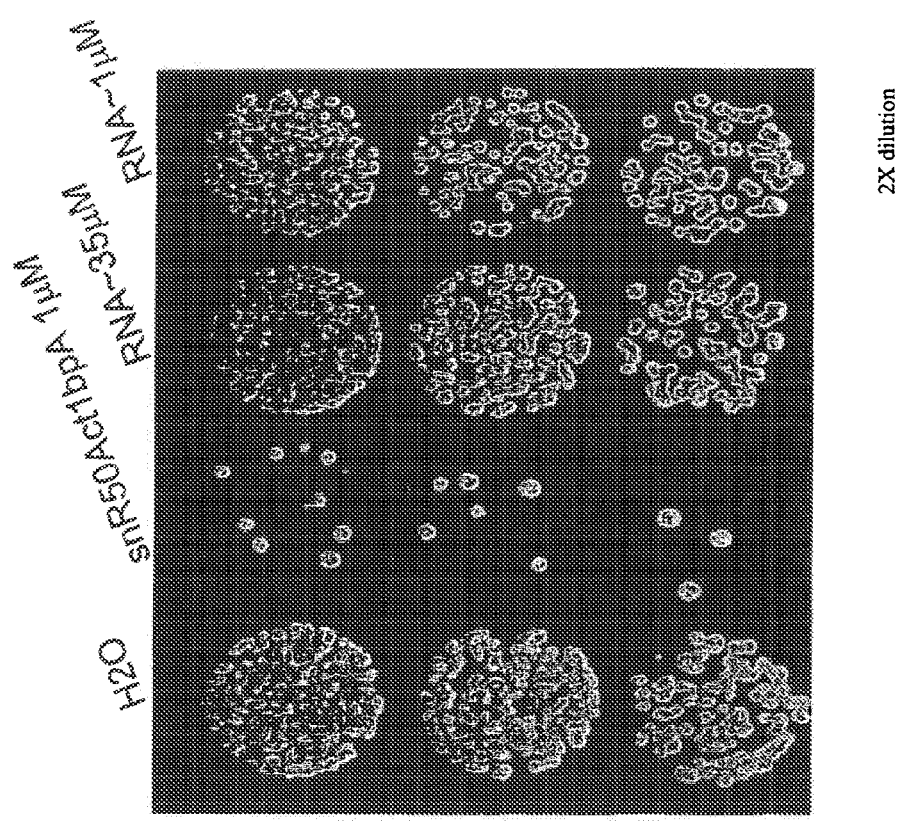

FIG. 12 shows the growth of yeast strains with or without an engineered guide RNA as described in Example 6.

FIG. 13 is a schematic showing the design of the His/Flag transcript and the overlap of oligos 1 and 2.

Figure 14:
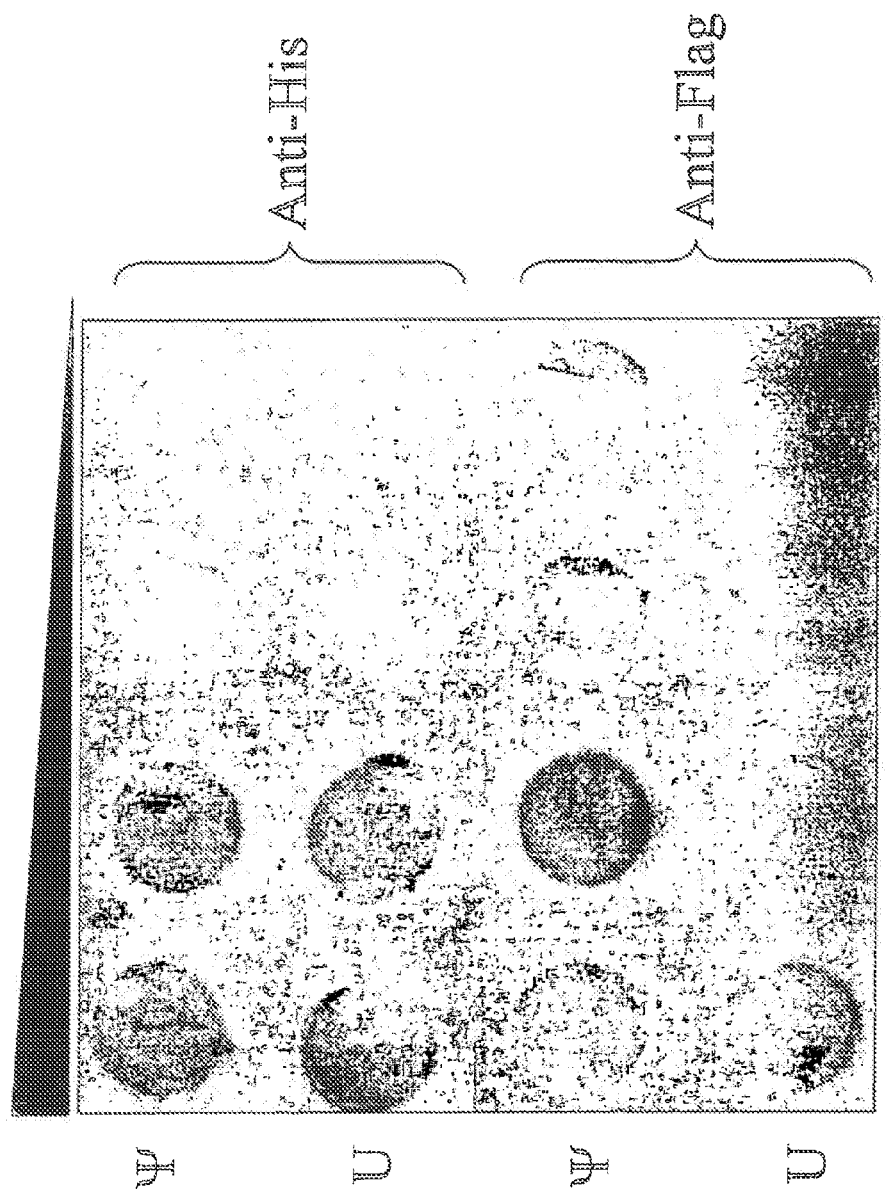

FIG. 14 shows a dot blot representing the blotting of the translation products of both the Ψ transcription product (lanes 1 and 3) and the U transcription product, as described in Example 11. In lanes 1 and 2, anti-His was used as the primary antibody. In lanes 3 and 4, anti-Flag was used as the primary antibody.

DETAILED DESCRIPTION OF THE INVENTION pre-mRNA splicing is, by definition, a post-transcriptional RNA processing reaction by which introns are removed from mRNA precursors and exons are precisely joined together to form functional mature mRNAs (Burge et al., *The RNA World*, p. 525, Cold Spring Harbor Laboratory Press, Cold Spring Harbor, 1999; Yu et al., *The RNA World*, p. 487, Cold Spring Harbor Laboratory Press, Cold Spring Harbor, 1999; Staley et al., Cell, 92:315, 1998). pre-mRNA splicing occurs via a two-step transesterification reaction pathway (FIG. 1). In the first step, the 2' hydroxyl group (2'-OH) of the branch point nucleotide adenosine attacks the phosphate at the 5' exon-intron junction (5' splice site), resulting in the cleavage of the phosphodiester bond between the 5' exon and intron and the concurrent formation of a new 5'-2' phosphodiester bond between the 5' end of the intron and the branch point adenosine. Thus, a lariat-structured intermediate (lariat intron-3' exon) and a cut-off 5' exon intermediate are produced. In the second step, the 3'-OH group of the cut-off 5' exon attacks the phosphate at the intron-3' exon junction (3' splice site), releasing the lariat intron product and generating the spliced mature mRNA product. According to this pathway, the 2'-OH group of the branch point adenosine is a key moiety that initiates the splicing reaction. In fact, when changed to 2'-deoxyadenosine, the branch point nucleotide is inactive in initiating the splicing, blocking the synthesis of mature mRNA in vitro (Query et al., Genes Dev., 8:587, 1994).

The two chemical reactions of pre-mRNA splicing shown in FIG. 1 occur only after the pre-mRNA is assembled into the functional spliceosome, a multi-component complex composed of five small nuclear RNAs (snRNAs U1, U2, U4, U5 and U6) and a large number of protein factors (Burge et al.; Yu et al.; Staley et al., supra). During spliceosome assembly, spliceosomal snRNAs and associated protein factors recognize and interact with the consensus sequences in the pre-mRNA, including the 5' and 3' splice sites and the branch site sequence, facilitating and specifying the transesterification reactions. Specifically, U1 (and perhaps protein factors as well) recognizes the 5' splice site (Zhuang et al., Cell, 46:827, 1986)., and the U2AF splicing factor (a heterodimer of 65 kDa and 35 kDa subunits) recognizes the 3' splice site, with the 65-kDa subunit interacting with the polypyrimidine tract and the 35-kDa subunit interacting with the invariant AG dinucleotide (Wu et al., Nature, 402:832, 1999). In addition to these interactions, US binds to the exon sequences at the 5' and 3' splice sites (Sontheimer et al., Science, 262:1989, 1993; Cortes et al, EMBO J, 12:5181, 1993; Wyatt et al., Genes Dev, 6:2542, 1992; Newman et al., Cell, 68:743, 1992;

Newman et al., Cell, 65:115, 1991), and U2 snRNA interacts, via base-pairing, with the branch site, bulging out the branch point adenosine to initiate the nucleophilic attack on the phosphate at the 5' splice site (the first chemical reaction) (Parker et al., Cell, 49:229, 1987; Zhuang et al., Genes Dev, 3:1545, 1989; Wu et al., Genes Dev, 3:1553,1989; Newby et al., Nat Struct Biol, 9:958, 2002). After the first step of splicing, the spliceosome undergoes additional conformational changes, leading to the second step of splicing. All the interactions occurring in the spliceosome are highly orchestrated, thus allowing for faithful and efficient splicing.

It is known that there is a consensus sequence required for splicing surrounding the branch site adenosine. While the vertebrate branch site consensus sequence YNYURAC (N can be any nucleotide and A is the branch point adenosine) is only loosely defined (Keller at al., Proc Natl Acad Sci USA, 81:7417, 1984; Zeitlin et al., Cell, 39:589, 1984; Ruskin et al., Cell, 38:317, 1984), the yeast branch site UACUAAC (the 3' most adenosine is the branch point nucleotide) is almost absolutely conserved (Langford et al., Cell, 33:519, 1983). The branch site sequence usually resides 20-40 nucleotides upstream from the 3' splice site (Keller et al.; Langford et al.; Zeitlin et al.; Ruskin et al., supra; Reed et al., Cell, 41:95, 1985). It is further known that specific mutations in the branch site sequence result in a total inhibition or a decreased level of pre-mRNA splicing.

As the branch site sequence is poorly defined in vertebrates, it is often difficult to identify the branch point by sequence inspection. To map the branch point nucleotide, a sufficient amount of spliced intermediate and product in the form of structured lariat RNA (lariat intron-exon 2 intermediate and lariat intron product) must be isolated. Subsequent analysis of these structured RNAs using primer-extension (the primer-extension product will stop one nucleotide before the branch point) or direct nuclease digestion (the branch structure is resistant to nucleases) allows for pinpoint identification of the branch point nucleotide (Ruskin et al., supra). However, while the branch point can be identified by these methods, it is almost always unpractical to obtain a sufficient amount of structured lariat RNA from cells. This is especially true in HeLa cell extract, where pre-mRNA splicing can be inefficient.

Figure 2:
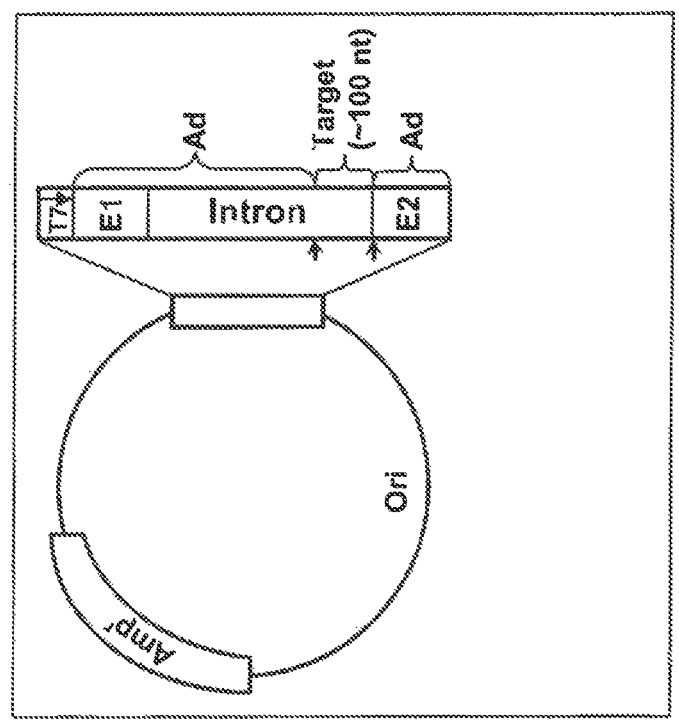
FIG. 2 shows a schematic of an embodiment of a plasmid of the invention that allows for highly sufficient mRNA splicing and identification of the branch point of a transcript.

It is an object of the present invention to provide a plasmid and method that allows for significant production of structured lariat RNA to facilitate the identification of the branch point of a pre-mRNA transcript. A preferred embodiment of a plasmid of the present invention is shown in FIG. 2. Preferably, the plasmid is constructed from pBluescript® II SK+ sold by Stratagene of La Jolla, Calif., but use of other plasmids is also contemplated. The plasmid shown in FIG. 2 contains an enhanced form of splicing substrate, a chimeric pre-mRNA under the control of the T7 promoter. The chimeric pre-mRNA contains the 5' and 3' exons and the first approximately ⅔ of the intron derived from the adenovirus standard splicing substrate, with the remaining ⅓ of the intron (approximately 100 nt), containing the branch point of interest to be determined. It is important to focus on the last ~100 nucleotides of an intron because the branch site is located about 20-40 nucleotides upstream of the 3' splice site (100 nucleotides will ensure the inclusion of the branch site).

In a preferred embodiment, the plasmid of the present invention is the plasmid of SEQ ID NO. 1. The plasmid of SEQ ID NO. 1 is based on the pBluescript® II SK+ with the exon and intron sequences from adenovirus shown in FIG. 2 cloned between the Xho I and BamHI restriction sites of the plasmid. This adenovirus sequence is represented as nucleotides 669-1034 of SEQ ID. NO. 1. The adenovirus sequence has a multiple cloning site where the approximately 100 nucleotide region of the intron of interest may be cloned, as follows (the number of the location of the site corresponds with the numbering of SEQ ID NO. 1):

EcoRI: 908
PmlI: 916
AgeI: 920
EcoRV: 928

Once the approximately 100 nucleotide region of the intron of interest is cloned into an appropriate cloning site, the branch point of the intron may be determined as described below.

Given that the adenovirus pre-mRNA is a strong splicing substrate, most of the substrate is spliced and a significant amount of lariat RNA is generated when assayed in HeLa nuclear extract or *Xenopus* oocytes (Yu et al., EMBO J, 17:5783, 1998; Zhao et al., RNA, 10:681, 2004). The 5' splice site of the adenovirus splicing substrate and the potential enhancer sequence within its exons are such particularly strong splicing elements that, upon fusion, they can convert a weak substrate to a strong substrate (Valcarcel et al., Nature, 362: 171, 1993).

For the purpose of convenience in building the chimeric pre-mRNA construct, a pre-mRNA gene cassette containing a unique restriction site in the intron region (~100 nucleotides upstream of the 3' splice site) and another unique restriction site in exon 2 (3 nucleotides downstream of the 3' splice site) will be generated (see FIG. 2).

To determine the branch point nucleotide of a pre-mRNA, a DNA fragment comprising the last ~100 nucleotides of its intron and the first three nucleotides of its 3' exon flanked by a corresponding restriction site at both ends will be generated by PCR. This product will readily replace its counterpart in the original cassette, generating a chimeric pre-mRNA gene, whose spliced lariat RNAs can then be used to determine the branch point nucleotide. A number of studies indicate that the in vitro splicing assay precisely recapitulates the process occurring inside cells, strongly suggesting that this assay will yield an accurate determination of the branch point nucleotide.

Other plasmids that allow for highly efficient splicing and production of structured lariat RNA are also contemplated by the present invention. A plasmid of the invention could contain 5' and 3' exons and all or part of an intron from other organisms to enhance splicing. Also, a plasmid of the invention could contain exons and introns from different organisms. Further, a plasmid of the invention could contain a promoter other than the T7 promoter. Importantly, the promoter to be used should be a promoter appropriate for the expression system chosen. It is most important that a plasmid of the invention allow for the production of sufficient quantities of structured lariat RNA to be able to determine the branch point.

In a preferred embodiment of a method to identify the branch point of a pre-mRNA, $^{32}$P-radiolabeled pre-mRNA will be generated via in vitro transcription with T7 polymerase using a plasmid described above, and will be directly subjected to the in vitro splicing assay by mixing it with HeLa nuclear extract or by injecting it into *Xenopus* oocytes. It is known that both splicing systems can generate stable lariat-structured RNAs in quantities sufficient for primer-extension and nuclease digestion analyses. Once a sufficient amount of structured lariat RNA is isolated, the branch point can be determined using techniques known in the art, such as by primer extension or direct nuclease digestion (Ruskin et al., supra).

The invention also contemplates affecting RNA processing by modifying RNA at other sites, either in combination with modification of the branch point, modification of other sites, or alone. Inspection of a large number of genes has also revealed several consensus sequences in introns at or near the 5' and 3' splice sites (Lerner et al., Nature, 283:220, 1980; Mount, Nucleic Acid Res, 10:459, 1982; Keller et al.; Langford et al.; Zeitlin et al.; Ruskin et al.; Reed et al., supra). The 5' splice site consensus sequence is G/GURAGU (/ represents the 5'exon-intron junction; R depicts a purine; the underlined dinucleotide GU is invariant) in vertebrate pre-mRNAs and G/GUAUGU in S. cerevisiae pre-mRNAs. The 3' splice site is YAG/G (here,/represents the intron-3' exon junction; Y is a pyrimidine; the underlined dinucleotide AG is invariant), which is frequently preceded by a CU-rich region in vertebrate pre-mRNAs. Further, there are potential other sites for modification, such as the polypyrimidine tract of an intron, and the codons of an axon, in particular the start and stop codons.

Figure 3:
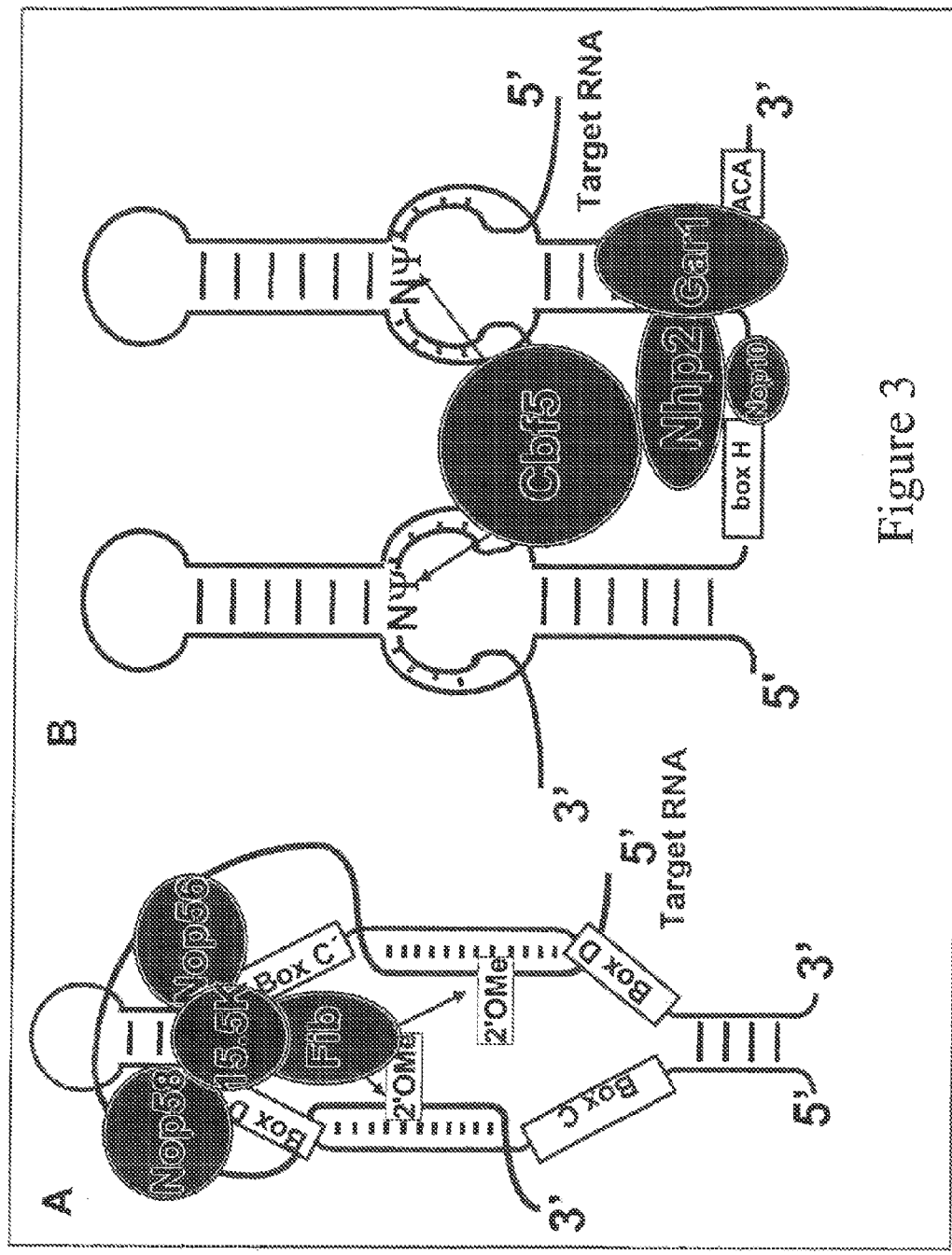
FIG. 3A shows a schematic of the Box C/D 2'-O-methylation complex.
FIG. 3B shows a schematic of the Box H/ACA pseudouridylation complex.

An embodiment of the present invention is a method of post-transcriptional gene silencing by targeted mRNA modification. In a preferred embodiment, targeted RNA modification is performed through RNA-guided RNA modification. RNA-guided RNA modification is facilitated by small nucleolar (sno) RNAs (Tycowski et al., Proc Natl Acad Sci USA, 93:14480, 1996; Steitz et al., Science, 270:1626, 1995; Kiss-Laszlo et al., Cell, 85:1077, 1996; Balakin, Cell, 86:823, 1996; Cavaille et al., Nature, 383:732, 1996). There are two types of snoRNAs, namely box C/D snoRNA and box H/ACA snoRNA (FIG. 3). Both types of RNA fold into a unique secondary structure, which is tightly associated with a common set of four core proteins (Fibrillarin, 15.5 kDa, Nop56 and Nop58 for eukaryotic box C/D type, and Cbf5, Nhp2, Gar1 and Nop10 for eukaryotic box H/ACA type) (FIG. 3).

Sequence inspection has revealed significant and uninterrupted complementarity between box C/D snoRNAs and ribosomal (r) RNAs, and a strong correlation between the locations of 2'-O-methylated residues in rRNAs and regions of snoRNA-rRNA complementarity led to the hypothesis that box C/D snoRNAs function as guides that direct 2'-O-methylation of rRNA (Bachellerie et al., Trends Biochem Sci, 20:261, 1995). Indeed, it was subsequently discovered that rRNA 2'-O-methylation always occurs in the residue base-paired to the nucleotide in snoRNA precisely 5 nucleotides upstream from box D (or D') (FIG. 3) (Kiss-Lazlo et al.; Cavaille et al., supra). Once the box C/D snoRNA finds its nucleotide target, fibrillarin, a methyl-transferase associated with the box C/D guide RNA, delivers the methyl group to the target nucleotide at the 2'-O position. The "Box D+5 rule" for predicting the site of 2'-O-methylation guided by snoRNAs has since been confirmed in various organisms including yeast, Xenopus and human, suggesting that RNA-guided 2'-O-methylation of rRNA is universal among eukaryotes (Smith et al., Cell, 89:669, 1995; Peculis, Curr Biol, 7:480, 1997; Kiss, EMBO J, 20:3617, 2001; Kiss, Cell, 109:145, 2002).

It has also been shown that box H/ACA snoRNA is responsible for guiding eukaryotic rRNA pseudouridylation, another major type of modification (Ni et al., Cell, 89:565, Ganot et al., Cell, 89:799). The guide sequences in box H/ACA RNAs are found in two segments in the linear RNA sequence that are brought together in internal loops within the hairpins (FIG. 3). Base-pairing between the bipartite guide sequence and the rRNA positions the target uridine at the base of the upper stem of the hairpin, leaving it unpaired within the so-called "pseudouridylation pocket" and located about 14-16 nucleotides upstream of box H or box ACA (FIG. 2).

When the target uridine is brought to the pocket, Cbf5, a pseudouridylase associated with the guide RNA [58], converts the uridine to pseudouridine. The snoRNA-guided pseudouridylation mechanism has been tested and verified in various systems (Ni et al.; Ganot et al., supra; Zebarjadian et al., Mol Cell Biol, 19:7461, 1999; Jady et al., EMBO J, 20:541, 2001; Zhao et al., RNA, 8:1515, 2002).

The methods of the invention are carried out through the use of engineered snoRNAs. For either of the guided modification mechanisms shown above, the snoRNA guide sequences can be modified to base pair with a sequence of the target RNA adjacent to the nucleotide to be modified. The engineered snoRNA guide sequences should be made to base pair with the appropriate sequence in the target RNA so that the nucleotide is in the proper position to undergo modification. For example, the guide sequence of the engineered RNA should allow a target RNA to hybridize with the engineered RNA such that the residue to be modified is at the "Box D+5" position.

In a preferred embodiment for gene silencing, the branch point adenosine of a pre-mRNA transcript is modified by 2'-O-methylation. The addition of a 2'-O-methyl (2'-OMe) group displaces the 2'-OH of the branch point adenosine required for mRNA splicing. Because the branch point adenosine is unable to attack the 5' exon-intron junction, splicing is not initiated, and a mature mRNA is not formed. The pre-mRNA transcript is then degraded without being translated, silencing the gene that encodes the transcript.

2'-O-methylation of the branch point allows for a highly reliable method of gene silencing. The 2'-OH of the branch point adenosine is the functional group that initiates the spicing process. As such, 2'-O-methylation is not a technique that decreases the efficiency of splicing, but should eliminate a transcript's capacity to splice altogether, preventing any "leak-through" splicing. All pre-mRNAs that are 2'-O-methylated at the branch point will be incapable of splicing. Further, although cryptic branch points are occasionally found, these branch points will be easily discovered during the determination of the branch point as described above. It will then be possible to account for a cryptic branch point and to possibly also deactivate it by modification.

A further embodiment of the invention is a method of selecting specific alternatively spliced variant of a transcript. When multiple branch points, corresponding to multiple splicing sites, are elucidated, a method of the invention can be used to modify the branch point involved in the splicing variant that is not desired. This way, only specific alternatively spliced variants will be expressed, allowing for study of alternative splicing. Methods for studying alternative splicing are of great importance, as approximately 50% of human genes are thought to be spliced. It is thought that alternative splicing is a major factor in providing for the diversity of proteins (approximately 90,000) generated by the comparatively small human genome (approximately 26,000 genes) (Ast, supra).

In a preferred embodiment for pre-mRNA or mRNA modification for purposes other than silencing, pseudouridylation is used to affect RNA processing. Pseudouridylation of a specific residue, targeted as described above, could be used to affect RNA processing.

Most preferably, the methods of the present invention are used to cause a uridine residue to be changed to pseudouridine in a nonsense (stop) codon. As set forth in Example 11 and FIG. 14, the inventors have unexpectedly found that the presence of pseudouridine ($\Psi$) in a stop codon can cause the translational machinery to read through the stop codon. The translation process is well known in the art and can be found in numerous biochemistry textbooks, including Chapter 30 of Biochemistry $2^{nd}$ edition by D. Voet and G. Voet, (John Wiley & Sons, Inc., 1995).

The stop codons of the genetic code are UAA, UAG and UGA. The methods of the present invention may be used to convert the U of the stop codon to Ψ, allowing the stop codon to be changed to a coding codon. This targeted modification can be done using the box H/ACA snoRNA mechanism described above. After the Ψ modification is made, the translational machinery will not stop at the modified codon, but instead will cause the anticodon of an aminoacylated tRNA to base pair with the modified codon, causing an amino acid to be added to the translated peptide chain and allowing translation to continue.

It is further contemplated that the pseudouridylation methods of the present may be used to modify the translation of other codons. As a non-limiting example, the codon AUU, encoding isoleucine, may be modified to AUΨ, which may cause the codon to encode methionine. Other potential codon modifications may be determined by using the genetic code.

It is also contemplated that pseudouridylation of residues could be used in the following non-limiting examples: 1) pseudouridylation of one or more uridines in the branch point or the consensus sequences near the 5' and 3' splice sites could be used to completely block or decrease the efficiency of mRNA splicing; 2) pseudouridylation of uridines in the poly-pyrimidine tract could be used to completely block or decrease the efficiency of mRNA splicing; and/or 3) pseudouridylation of uridines in the start codons or stop codons of mRNAs could be used to decrease or increase the efficiency of translation of the modified mRNA. It is further contemplated that a single pseudouridyl modification can be performed in an RNA sequence, or that a pseudouridyl modification can be performed in combination with other pseudouridyl modifications, or in combination with other modifications, such as branch point modifications.

It is also contemplated that other RNA modifications may be used to affect the translation and/or processing of pre-mRNA or mRNA. As a non-limiting example, it is also contemplated that 2'-O-methylation may be used in a manner analogous to those described for Ψ above, for example, the 2'-O-methylation of a residue in a stop codon.

Further, it is contemplated that the methods of the invention may be performed on both pre-mRNA (unspliced mRNA) or mRNA (spliced mRNA), and the terms may be used interchangeably herein, unless otherwise noted. It is still further contemplated that modifications may be made in any type of coding RNA, regardless of its characteristics or state of modification or processing.

In an embodiment of the invention, the methods of mRNA modification are used for therapeutic treatment of a mammal. In a preferred embodiment of the invention, a DNA sequence encoding an engineered snoRNA can be delivered to a patient using standard gene therapy methods. The DNA encoding the engineered snoRNA will then be present in the cells of the patient, either integrated into the patient's genome or present as an autonomous plasmid or vector. This DNA sequence can then be transcribed to produce functional engineered snoRNA in the desired cells of the patient, causing the silencing or modification of the target transcript. In a preferred embodiment, the DNA sequence encoding the engineered snoRNA is a viral vector capable of transfecting the cells of interest.

The therapeutic methods of the present invention may be used to treat or prevent a wide variety of ailments. These ailments may be treated by causing the modification of pre-mRNA or mRNA in a patient. Non-limiting examples of ailments that may be treated or prevented include: a genetic disease, a CNS disease; an inflammatory disease; a neurodegenerative disease; a cardiovascular disease; an autoimmune disease; and cancer. The genetic diseases to be treated include, but are not limited to, amyloidosis, LINCL, hemophilia, Alzheimer's disease, atherosclerosis, giantism, dwarfism, hypothyroidism, hyperthyroidism, cystic fibrosis, aging, obesity, Parkinson's disease, Niemann Pick's disease, cystic fibrosis, familial hypercholesterolemia, retinitis pigmentosa, Duchenne muscular dystrophy, or Marfan syndrome. For prevention or treatment of a disease, especially a genetic disease, it is contemplated that the therapeutic methods of the present invention may also be coupled with a genetic test, to help pinpoint a specific region of the pre-mRNA or mRNA to be modified. As a non-limiting example, DNA sequencing could be used to determine a nonsense codon which could then be targeted for modification.

In another embodiment of the invention, the methods for gene silencing by mRNA modification are used for in vivo laboratory studies. The invention is particularly well suited to silencing genes in cultured cells, including, but not limited to, mammalian cells, *Xenopus* oocytes and yeast cells. Engineered snoRNAs can be delivered to cells using the gene therapy methods described above or the engineered RNAs can be directly injected or otherwise introduced to cells.

Importantly, the gene silencing methods of the invention allow for modification within the intron of the transcript to be silenced. This is especially important for in vivo laboratory studies, where it is desirable to be able to provide the gene being silenced on a plasmid to rescue a phenotype observed through silencing. Because the invention only affects genes containing introns, it allows for phenotype rescue by providing a mutant version of target gene in which the target sequence (e.g. the branch site region) is mutated or an intonless version of the target gene. This is in direct contrast to RNAi methods, which target exon sequences, and hence silence all types of transcripts, including those provided for phenotype rescue.

It should be apparent that there are uses for the invention other than those described above. Such other uses include, but are not limited to, other modifications of the branch site not disclosed above and the use of other systems for performing the modifications, either RNA guided or non-RNA guided, such as non-RNA guided protein catalyzed modifications.

EXAMPLES

Example 1

A Small Nucleolar RNA (snoRNA) Guides U2 snRNA Pseudouridylation in *S. cerevisiae*

Yeast U2 snRNA contains three pseudouridines (Ψ35, Ψ42 and Ψ44, which are equivalent to Ψ34, Ψ41 and Ψ43 in vertebrate U2 snRNA) within or near the branch site recognition region. It was previously shown that the formation of Ψ35 and Ψ44 is catalyzed by the protein enzymes Pus7p and Pus1p, respectively (Ma et al., EMBO J, 22:1889, 2003; Massenet, et al., Mol Cell Biol, 19:2142, 1999), but the mechanism for catalyzing Ψ42 formation was unknown. By analogy, it was widely believed that Ψ42 formation was also catalyzed by a protein enzyme alone, in the same manner as eukaryotic tRNA modifications. Given our access to the yeast GST-ORF fusion protein library (Phizicky, Methods Enzymol., 350:546, 2002), we screened for the enzyme for this remaining pseudouridine. Surprisingly, an activity screen identified a Ψ42-specific pseudouridylase activity that was associated with Nhp2p, one of the four core protein components of Box H/ACA sno/scaRNPs (see FIG. 3). However, recombinant Nhp2p alone had no activity, suggesting that a Box H/ACA sno/scaRNP, including several proteins and a guide RNA, might be involved in Ψ42 formation. Indeed, the other Box H/ACA sno/scaRNP proteins, when isolated by tandem affinity purification (TAP), copurified with the pseudouridylase activity. To directly test whether a Box H/ACA sno/scaRNA is required for the activity the TAP preparations (e.g., Gar1-TAP-tagging preparation) were treated with micrococcal nuclease, yielding preparations devoid of pseudouridylase activity. The activity was restored, however, upon subsequent addition of RNAs extracted from TAP preparations, demonstrating a requirement for Box H/ACA sno/scaRNA.

To identify the box H/ACA sno/scaRNA, total Box H/ACA RNA isolated from the Gar1p-TAP-tagging preparation was gel-fractionated. Individual fractions were then added to the micrococcal nuclease-treated Gar1p-TAP-tagging preparation to test their ability to reconstitute pseudouridylation in vitro. One RNA fraction (~180-200 nucleotides) was successful in this regard, suggesting that the Ψ42-specific guide RNA was present in this fraction. However, it appeared that there were many different Box H/ACA RNAs in this fraction, as a smeared polyacrylamide gel signal ranging ~180-200 nucleotides was observed when the RNA fraction was 3'-labeled with [$^{32}$P]pCp. To isolate the Ψ42-specific RNA, an RNA library using this particular RNA fraction and the "tailing-RT-PCR-cloning" method was constructed. Individual RNAs derived from the library for guide activity were then screened using the reconstitution system. Somewhat surprisingly, the Ψ42-specific guide RNA was identified as snR81, a genuine box H/ACA snoRNA most recently identified as a guide for 25S rRNA pseudouridylation at position 1501. Apparently, the 5' pseudouridylation pocket is specific for Ψ42 of U2, and the 3' pocket is specific for Ψ1501 of 25S rRNA.

To demonstrate that the pseudouridylase activity is in fact dependent on snR81 snoRNA and the Box H/ACA sno/scaRNP proteins in vivo an snr81-deletion strain and nhp2 or cbf5 conditional depletion strains (all core box H/ACA sno/scaRNP proteins are essential for growth) were constructed or a slow-growth cbf5 point mutation strain was used. The results indicated that the conversion of U42 to Ψ42 in yeast U2 is indeed catalyzed by snR81 snoRNP via an RNA-guided mechanism, which differs from the previously identified protein-only mechanism catalyzing yeast U2 pseudouridylation at the other two positions, Ψ35 (Ma et al., supra) and Ψ44 (Massenet et al., supra). As expected, subsequent localization studies detected snR81 guide RNA exclusively in nucleoli; no signal was detected in the nucleoplasm or nucleolar bodies, which are distinct yeast intranuclear bodies equivalent to Cajal bodies in higher eukaryotes. These data thus indicated for the first time that spliceosomal snRNA pseudouridylation can be catalyzed by an RNA-dependent mechanism as well as an RNA-independent mechanism, and that a Box H/ACA snoRNA can guide both spliceosomal snRNA (nucleoplasmic) and rRNA (nucleolar) for pseudouridylation.

Example 2

Artificial Box H/ACA RNAs can Guide Yeast U2 snRNA Pseudouridylation at Novel Sites In Vivo On the above data showing that snR81 box H/ACA snoRNP catalyzes U2 pseudouridylation at position 42, the possibility that artificial guide RNAs, when introduced into yeast, can guide the pseudouridylation of U2 and perhaps the other spliceosomal snRNAs at novel sites was further explored. This method would not only prove that the artificial guide RNA is in fact functional, but also provide a powerful tool for functional analyses of spliceosomal snRNA modifications.

Figure 4:
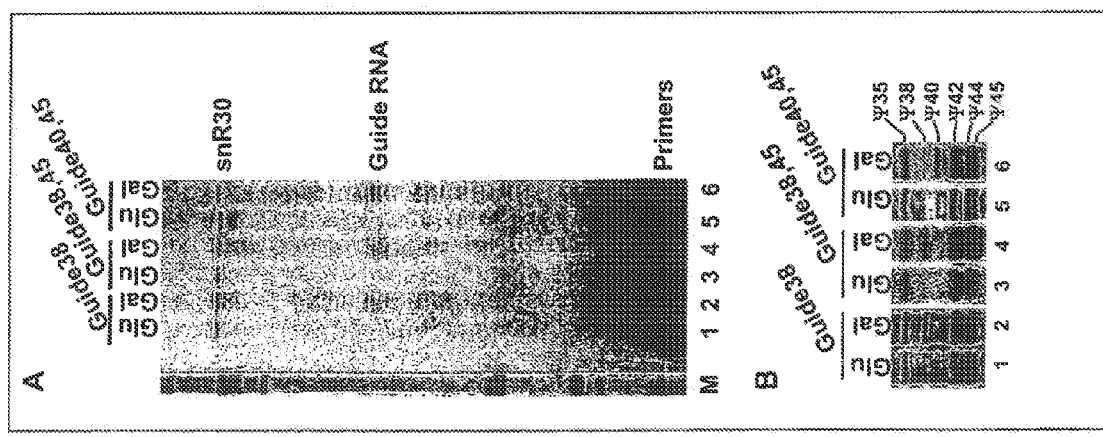
FIGS. 4A and 4B show polyacrylamide sequencing gels as showing the location of modified pseudouridyl residues in target mRNAs as described in Example 2.

It was first tested whether an artificial U2 pseudouridylation-specific guide RNA could be expressed in yeast and whether its expression could direct U2 pseudouridylation at targeted novel positions. Several plasmids were constructed, each containing one or two artificial box H/ACA RNAs derived from a *Xenopus* box H/ACA snoRNA, in which the guide sequences were altered to target Ψ38, Ψ40 or/and Ψ45 of yeast U2 snRNA (these three sites are not modified in yeast U2). The expression of the artificial guide RNAs was under the control of the $P_{GAL}$ promoter. After transformation, yeast cells were grown first in glucose-containing medium and then switched to galactose-containing medium. Total RNA was recovered before and after the medium switch, guide RNA expression was assessed by primer-extension analysis, and U2 snRNA pseudouridylation was analyzed by CMC modification followed by primer-extension. As shown in FIG. 4A, the guide RNA was not expressed in cells grown in glucose medium (lanes 1, 3 and 5). However, after the medium switch, the guide RNA was expressed at adequate levels (lanes 2, 4 and 6). Preliminary primer-extension results showed that the expression level of mature guide RNA (after cleavage of extra sequences from the 5' and 3'ends) was roughly comparable to other snoRNAs, such as snR30, at about 1000 copies per cell (FIG. 4A).

A pseudouridylation assay indicated that U2 snRNA isolated from cells grown in glucose medium contained only three naturally occurring pseudouridines, Ψ35, Ψ42 and Ψ44 (FIG. 4B, lanes 1, 3 and 5). However, after the medium switch, additional pseudouridine signals were observed in yeast U2 snRNA (FIG. 4B, lanes 2, 4 and 6). Although not quantitative, the signals of new pseudouridines were comparable to that of the naturally occurring pseudouridines, suggesting a similar level of modification. The formation of new pseudouridines was absolutely dependent on the expression of the appropriate artificial guide RNAs. These preliminary results demonstrated the efficacy of our new method.

Example 3

Evidence that Guide RNAs can Direct mRNA (or Pre-mRNA) Modification

Based the fact that snR81 snoRNA guides the pseudouridylation of two types of RNA (U2 snRNA and 25S rRNA) in yeast (C1), and that an artificial box H/ACA guide RNA, once introduced into yeast, can direct U2 snRNA pseudouridylation at desired sites (C2), it was explored whether mRNAs/pre-mRNAs are also modified, an issue that has been ignored for many years.

Now that the RNA-guided mechanism has been identified in eukaryotic (and Archael) cells (Yu et al., *Topics in Current Genetics*, p. 223, Springer Verlag, New York, 2005), it is easier to study mRNA modifications in detail. A number of mRNA targets for any individual guide RNA can be easily identified using sequence alignment. The question is whether they are, in fact, modified. One might doubt the existence of mRNA modifications for a number of reasons. Perhaps the most compelling reason is that guide RNPs and mRNAs are localized in different subnuclear compartments (mRNA is temporarily in the nucleoplasm and most guide RNPs are reported in either Cajal bodies or nucleoli). This differential localization argues against mRNA modifications. However, there are a number of points that support the notion that mRNA might be modified. Although mRNAs and the guide RNPs localize to different subnuclear compartments, their localization does not necessarily reflect the subnuclear site(s) in which modification truly occurs. In fact, many RNAs and proteins are quite mobile (Gall, Nat Rev Mol Cell Biol, 4:975, 2003; Gall, FEBS Lett, 498:164, 2001; Bertrand, Prog Mol Subcell Biol, 35:79, 2004), and they travel between subnuclear compartments and even between the nucleus and cytoplasm. For instance, the spliceosomal Sm snRNPs cycle through the cytoplasm during maturation (at least in *Xenopus* oocytes) Mattaj, *Structure and Function of Major and Minor Small Nuclear Ribonucleoprotein Particles*, p. 100, Springer-Verlag Press, Heidelberg, 1988). It has been shown that at any given time various RNAs (spliceosomal snRNAs/pre-snRNAs, tRNAs/pre-tRNAs, etc.) are detected in nucleoli and/or Cajal bodies (Yu et al., J Cell Biol, 152:1279, 2001; Steeman, Exp Cell Res, 243:290, 1998; Lange, Mol Biol Cell, 11:2419, 2000; Narayanan, Mol Biol Cell, 10:2131, 1999; Thompson et al., Science, 302:1399, 2003; Bertrand et al., Genes Dev, 12:2463, 1998; Stanek et al., J Cell Biol, 166, 1015; Gerbi et al., Mol Biol Cell, 13:3123, 2002; Frey et al., J Cell Biol, 154:499, 2001; Smith et al., Mol Biol Cell, 11: 2987, 2000; Verheggen et al., EMBO J, 21:2736, 2002; Verheggen et al., EMBO J, 20:5480, 2001; Speckmann et al., Mol Cell Biol, 19:8412, 1999). In addition, the guide RNPs, although concentrated in Cajal bodies and nucleoli, are probably present in the nucleoplasm as well, where they may be too sparse to detect. Consistent with this notion, it was found that a *Xenopus* guide RNA might localize predominantly in the nucleoplasm (Zhao et al., supra). In another case, a spliced leader RNA (SL RNA)-specific guide RNA was also localized in the nucleoplasm (Liang et al., RNA, 8:237, 2002). The snR81 snoRNP, which is detected in the nucleolus but not the nucleolar body (equivalent to Cajal body in higher eukaryotes), catalyzes both U2 snRNA and rRNA pseudouridylation (C1), thus arguing strongly that either the modifying enzyme (snR81snoRNP) or its non-nucleolar substrate (U2) must travel. Even more compelling are recent data from Huttenhofer's group suggesting that a brain-specific mRNA is perhaps 2'-O-methylated by a brain-specific box C/D snRNP Cavaille, et al., Proc Natl Acad Sci USA, 97:14311, 2000). However, it should be noted that the low abundance of mRNAs has made it extremely difficult to analyze their modification.

Figure 5:
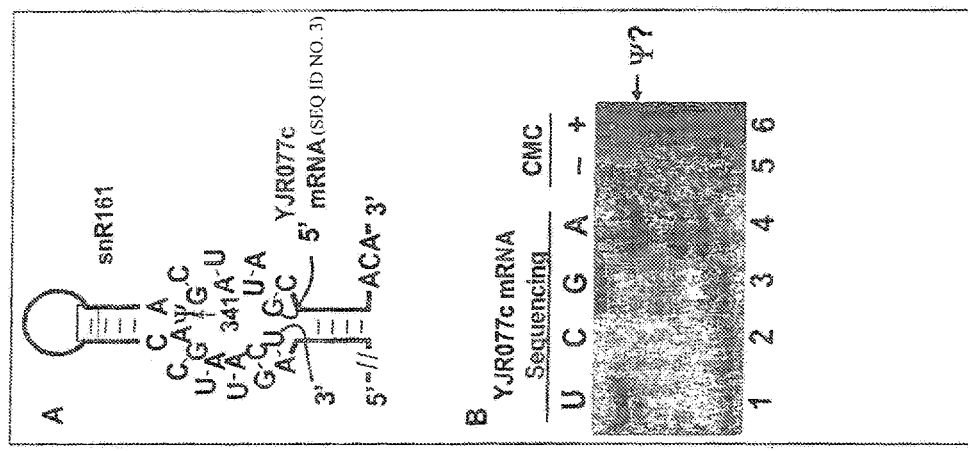
FIG. 5A shows a schematic of the predicted site of pseudouridylation in the mRNA transcript encoded by the yeast gene YJR077c (SEQ ID NO. 3).
FIG. 5B shows a polyacrylamide sequencing gel showing a primer extension experiment as described in Example 3.

As a first step towards the goal of understanding mRNA/pre-mRNA modification, yeast biochemical analysis was used to detect mRNA modifications. Although there are problems with low abundance, a large quantity of yeast cells can be grown to offset this. In addition, relatively abundant genes were chosen for analysis. Based on the snR161 box H/ACA guide RNA prediction, YJR077c mRNA is probably pseudouridylated at position 341 (relative to its start codon) (FIG. 5A). Total RNA isolated from a large volume of yeast cell culture was subjected to the pseudouridylation assay (CMC modification followed by primer-extension). Our preliminary results (FIG. 5B) showed that Ψ-specific CMC modification clearly generated a primer-extension stop at the predicted site (lane 6). In contrast, no stop was detected in the control sample in which no CMC was used (lane 5). This result bolsters the case for mRNA modification and is an encouraging sign for artificially targeting a relatively abundant mRNA-encoding gene for modification.

Example 4

Expression of a Box C/D RNA Targeting the Branch Point Adenosine of ACT1 Pre-mRNA Results in a Growth Defect Phenotype ACT1 is an essential gene in *S. cerevisiae*, and its deletion impairs growth. The splicing of ACT1 pre-mRNA has been extensively studied in yeast, and thus it was chosen as a target for our analysis. To target the branch point adenosine for 2'-Omethylation ($A_{259}$ relative to the 5' splice site), a new box C/D guide RNA was derived from snR50, a natural yeast box C/D RNA responsible for the 2'-O-methylation of 25S rRNA at position 867 (Lowe et al., Science 283:1168-1171). In the new box C/D guide RNA (referred to as Act-BP-Guide thereafter), the original guide sequence upstream of the D box was changed to perfectly match the branch point sequence of the ACT1 pro-mRNA, precisely positioning the branch point adenosine for 2'-O-methylation (5 nucleotides upstream of the D box) (FIG. 6A). The sequence encoding Act-BP-Guide was inserted into a vector, and the RNA expression was controlled by the Gal promoter (FIG. 6A).

Upon transformation with the Act-BP-Guide plasmid (pAct-BP-Guide), a purified single colony (through re-streaking on glucose (SD) medium) was plated on either SD or galactose (SGal) medium. As shown in FIG. 6B, yeast cells grew well in SD medium but failed to grow in SGal medium. As a control, cells transformed with vector alone showed no difference in growth on either medium (FIG. 6B).

Example 5

Act-BP-Guide can Direct the 2'-O-Methylatation of ACT1 Pre-mRNA at the Target Site The fact that expression of Act-BP-Guide in SGal caused cell death suggested that Act-BP-Guide might indeed direct the 2'-O-methylation of ACT1 pre-mRNA at the branch point adenosine (FIG. 6A). To verify the 2'-O-methylation at the target site, an in vitro 2'O-methylation assay was performed using a short RNA substrate corresponding to the ACT1 branch site sequence. This substrate contained a single $^{32}$P 5' of the branch point adenosine, and it was incubated in the presence of S-adenosyl methionine with yeast extracts prepared from cells transformed with pAct-BP-Guide or vector alone. The singly radiolabeled RNA substrate was then gel purified and subjected to nuclease P1 digestion and TLC analysis.

Figure 7A:
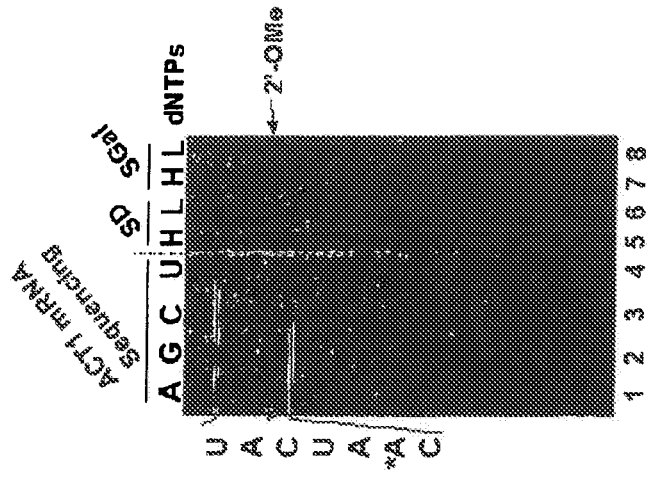
FIG. 7A shows an in vitro 2'-Omethylation assay. A short RNA corresponding to the ACT1 pre-mRNA branch site sequence was singly labeled with $_{32}$P at the branch point (5' of the branch point adenosine). It was incubated with extracts prepared from pAct-BP-Guide-transformed cells that had been grown in SD or SGal. After incubation, the RNA substrate was purified and subjected to RNase P1 digestion and TLC analysis. Lanes 1 and 2 are the makers of 5'-$_{32}$pA (adenosine 5' monophosphate), and 5'-$_{32}$pAm (2'-O-methylated adenosine 5'monophosphate), respectively. Lanes 3 and 4 are modification reactions in which extracts were prepared from SD-cultured (lane 3) or SGal-cultured (lane 4) cells. Lanes 5 and 6 are controls where extracts were prepared from cells containing no pAct-BP-Guide. The positions of adenosine 5' monophosphate (5'-pA) and 2'-O-methylated adenosine 5' monophosphate (5'-pAm) are indicated.

As shown in FIG. 7A, extracts prepared from SD-cultured cells, which had been transformed with pAct-BP-Guide, failed to convert the branch point adenosine into a 2'-O-methylated nucleotide (lane 3). In contrast, when the extracts prepared from SGal cultured cells were used, a 2'-O-methylated branch point adenosine was observed (lane 4). As a control, no 2'-O-methylation activity was detected in extracts prepared from cells transformed with vector alone (lanes 5 and 6). These results suggest that Act-BP-Guide indeed directed the site-specific modification.

To confirm the specific guide activity of Act-BP-Guide, the 2'-O-methylation of endogenous ACT1 pre-mRNA was directly checked using a standard primer extension-based assay$_{15}$. It is well established that during primer-extension, reverse transcriptase (AMV-RT) will pass through the 2'-O-methylated residues contained in the template RNA under high concentrations of dNTPs; however, under low concentrations of dNTPs, primer-extension will stop/pause one nucleotide before the 2'-O-methylated residues, thus allowing the identification of a 2'-O-methylated residue(s) within the template RNA (Madden et al., Biochimic 77:22-29, 1995).

Figure 7B:
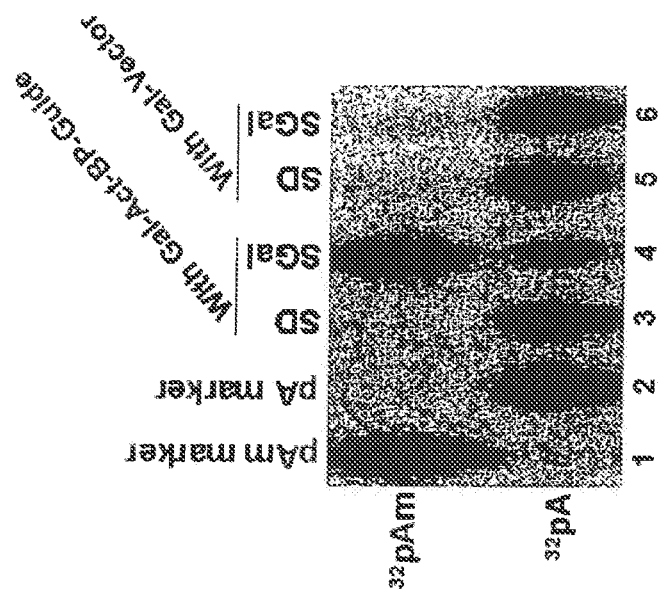
FIG. 7B shows 2'-O-methylation of endogenous ACT1 pre-mRNA. Total RNA isolated from Act-BP-Guide-transformed cells was subjected to primer-extension at high (H, 1 mM, lanes 5 and 7) or low (L, 0.004 mM lanes 6 and 8)

As shown in FIG. 7B, when total RNA isolated from yeast grown in SD was used
as template, primer-extension did not produce any stop/pause under either high or low concentrations of dNTPs (lanes 5 and 6). In contrast, when total RNA was isolated from cells incubated in SGal (overnight incubation after medium switch from SD to SGal), primer-extension resulted in a clear stop/pause under the low concentration of dNTPs (lane 8); as expected, however, no stop/pause was observed under the high concentration of dNTPs (lane 7). The stop/pause band lined up with the residue one nucleotide upstream of the branch point adenosine (FIG. 7B), indicating that the branch point adenosine was in fact 2'-O-methylated. Thus, it can be concluded that Act-BP-Guide, upon induced expression in the cell, can guide the 2'-O-methylation of ACT1 pre-mRNA at the branch point adenosine.

Example 6

Act-BP-Guide Drastically Reduces the Level of ACT1 Mature mRNA

To understand the molecular basis of the deleterious effect of Act-BP-Guide on yeast cell growth, the levels of mature ACT1 mRNA were measured in yeast strains expressing or not expressing Act-BP-Guide using several standard assays.

FIG. 8A shows the primer-extension analysis. Under an un-induced condition (in SD medium), no Act-BP-Guide was detected (lane 1), and a high level of ACT1 mRNA was present, as expected (lane 1). Remarkably, however, when induced (in SGal medium), Act-BP-Guide was expressed (lane 2), resulting in a drastic reduction in ACT1 mRNA level (lane 2). As a control, a similar level of constitutively expressed U2 snRNA was detected in cells under either condition (compare lane 1 with 2). FIG. 8B shows an RNase protection assay. Again, ACT1 mRNA was detected only under un-induced conditions (SD) (lane 1) but not under induction conditions (SGal) (lane 2). When a nontarget mRNA (Urp1 mRNA) was assayed, a similar expression level was detected under either condition. Finally, northern analysis was used to detect ACT1 mRNA (FIG. 8C).

As expected, we detected ACT1 mRNA when the cells were grown in SD (lane 1) but not in SGal (lane 2). When the same gel was stained with ethidium bromide, similar levels of rRNA (25S and 18S) were detected under both conditions (compare lane 3 with lane 4). These results indicate that the ACT1 mRNA level was indeed drastically reduced in response to the expression of Act-BP-Guide.

Example 7

Splicing Uses Only the Branch Point and not its 5'-Adjacent Adenosine

Given that the branch site (UACUAAC) is extremely conserved in yeast premRNA, and to some extent in higher eukaryotic pre-mRNA (YNYURAC) as well, it is of great interest to delineate the branch point adenosine used in splicing. Using HeLa nuclear extracts, Query et al. (Genes Dev. 8:587-597, 1994) demonstrated that either the 3'-most adenosine or its 5'-adjacent purine can serve as the branch nucleotide for the first step of splicing; however, only the 3' adenosine goes through two transesterification reactions, generating spliced mRNA. In contrast, two adenosines in the branch site of nematode pre-mRNA can be equally used as the branch point nucleotide when tested in a cell-free system (Hannon et al., Cell 61:1247-1255, 1990). In yeast, however, it is not yet clear as to whether one or both of the 3'-most adenosines within the branch site can be used as the branch point nucleotide.

The results presented above suggested that only the 3'-most adenosine served as a functional branch point nucleotide, because 2'-O-methylation at this adenosine almost completely blocked production of ACT1 mRNA. To confirm this results, two new guide RNAs, were designed each targeting the adenosine 5' adjacent to (−1) or two nucleotide downstream (+2) of the branch point nucleotide of ACT1 pre-mRNA (FIG. 9A). When transformed with the plasmids containing the guide RNA gene under the control of the Gal promoter, yeast cells did not show any growth defect phenotype on SGal (FIG. 9B).

The modification assay indicated that the target adenosine was indeed 2'-O-methylated under the same conditions (FIG. 9C, lanes 2 and 4). Yet, the level of mature ACT1 mRNA was not altered in these SGal-cultured cells (FIG. 9D, lanes 2 an 6) compared to that in SD-cultured cells (lanes 1 and 5) or to that in the strains transformed with insert free vector (data not shown). As expected, however, ACT1 mRNA level was drastically reduced when cells expressed Act-BP-Guide (FIG. 9D, lane 4). These results clearly indicate that the splicing of the yeast ACT1 pre-mRNA utilizes only the 3'-most adenosine within the branch site sequence as the branch point nucleotide. Because the two new guide RNAs, while targeting the other adenosines in the same region, maintained almost identical complementarity, the results also suggest that the effect of targeting the branch point adenosine was truly 2'-O-methylation-specific rather than an antisense effect (i.e., modification requires a long stretch of base pairs between the guide and target sequences).

Example 8

Co-Expression of an Intron-Less ACT1 Gene Rescues the Growth Phenotype

Although Act-BP-Guide was designed to target the branch point nucleotide of ACT1 pre-mRNA, it remained necessary to verify the target specificity. The strain that carried pAct-BP-Guide was transformed with a second plasmid containing an intron-less ACT1 gene, expression of which was also under the control of the Gal promoter. As a control, a plasmid bearing an intron-containing ACT1 gene was also introduced into the same strain. Upon transformation, the cells were streaked on either SD or SGal in parallel.

As shown in FIG. 10, when the intron-less ACT1 gene was expressed, the cells grew as healthy in SGal as in SD. However, the expression of the intron-containing ACT1 gene failed to rescue the growth phenotype-no growth was detected on SGal. These results thus demonstrated the specific effect of Act-BP-Guide on actin gene expression.

Example 9

Fluorescently-Labeled Guide RNA can be Taken Up by Yeast Cells

Guide RNA targeting the branch point as described above was in vitro transcribed with amino allyl UTP and purified on an urea-PAGE gel. Purified RNA was precipitated with ethanol 3 times. 5 μg of RNA was dissolved in 70 μL 0.1M NaHCO$_3$, pH 8.8 and mixed with 30 μL DMSO containing 0.5 mg Oregon Green 488 dye. Samples were wrapped in aluminum foil and incubated with gentle shaking for 24-48 h. Fluorescently labeled RNA was then purified by precipitation three times.

Yeast cells were grown in YPD medium to an OD of approximately 2.0. Cells were harvested, spun down, and resuspended in fresh YPD to an OD of approximately 2.0. Fluorescently labeled guide RNAs at a final concentration of 1 μM was added to the cell culture and incubated with gentle shaking overnight at 30° C. 1 μL of cell culture was taken, diluted 1000 times, and spotted to YPD solid media, followed by incubation at 30° C. until the appearance of colonies.

As shown in FIG. 11, the fluorescently labeled guide RNA was taken up by the yeast cells.

Example 10

A Guide RNA Targeting the Branch Point of ACT1 Pre-mRNA Inhibits Yeast Cell Growth when Added Exogenously Guide RNA targeting the branch point (snR50Act1bpA) was incubated with yeast cells, along with controls containing only water or different concentrations of non-specific RNA, were incubated with yeast cells as described in Example 9. Cells were then plated on solid galactose medium and incubated at 30° C. until the appearance of colonies. As seen in FIG. 12, cells incubated with guide RNA snR50Act1bpA exhibited a growth phenotype consistent with the silencing of actin1 shown above, while all controls grew normally. These data suggest that yeast genes may be silenced by adding engineered guide RNAs exogenously.

Example 11

The Translation Machinery Reads Through a ΨAA Stop Codon

To determine the effects of pseudouridylation on the stop codon, mRNA transcripts were made with either U or Ψ as a transcription substrate.

A T7 template for transcription was prepared by a normal PCR reaction. Two oligos were used for PCR. The oligos have over-lapping at 3' end as shown in FIG. 13. As can be seen in FIG. 12, the template encodes a His-tag upstream of the stop codon TAA and a Flag-tag downstream of the same stop codon. Because of the design of the template, a Flag-tag will only be present in the final translation product if the stop codon is read through.

The transcription reaction system used was ordered from Biolab (catalog no. M0251 S). The reaction mixture for making RNA for translation is 200 μl of: 1× RNA pol reaction buffer, 100 ug/ml BSA, 500 μM each of ATP GTP, CTP and UTP or ΨTP, 1000 Uint/ml T7 RNA polymerase and 100 μg/ml of PCR DNA template. The mixture was incubated at 37° C. for 1.5 hours. U or Ψ containing RNAs were PAGE-Urea gel purified.

The U or Ψ containing RNAs were translated using Novagen's "Red Nova Lysate" (catalog no. 69360-4) mixed as follows:

| 2 μl | 12.5X translation Mix with all amino acids (combine three mixtures at 1:1:1) |
| 1 μl | 2.5M KAc |
| 0.5 μl | 25 mM MgAc2 |
| 2 μl | U or Ψ RNA (1 μg/μl) |
| 9.5 μl | H2O |
| 15 μl | Total volume |

Ten μl of lysate was added to start the reaction which was incubated at 30° C. for 60 min. After incubation, SDS was added to 0.1% and the mixture was heated at 95° C. for 2 min. Samples were then chilled on ice for 1 min. The samples were spun at 13000 rpm for 5 min, and the supernatant was collected for analysis.

The U and Ψ samples were dotted on an NC membrane. Each sample was dotted four times with 5× dilution ratio between dots. The dotting was duplicated on another membrane. Both membranes were dried and exposed to UV light at 12000 μJ/cm2.

One membrane was used for western blotting with anti His-Tag antibody and the other for western blotting with anti-Flag antibody. The primary antibody was anti-His or anti-Flag Mouse IgG, respectively. The secondary antibody was Anti-Mouse IgG antibody conjugated with alkaline phosphatase for each blot. The developing system used was NBT&BCIP manufactured by Promega (catalog no. S380C&S381C).

Briefly, the western blots were performed as follows. The membranes were blocked in a 5% non-fat milk-TBST solution (10 mM Tris-HCl, 0.15 M NaCl, 8 mM sodium azide, 0.05% tween-20, pH 8.0) for 30 min. The membranes were then hybridized with their respective first antibodies at room temperature for 30 min with shaking. The membranes were washed twice with TBST for 5 min. Diluted alkaline-phosphatase conjugated secondary antibody was added and incubated for 30 minutes at room temperature with gentle shaking. The membranes were again washed twice with TBST for 5 min at room temperature. 500 μl of BCIP/NBT substrate was added and the membranes were allowed to stand until dots began to appear. The membranes were rinsed with water to stop the developing.

The results of the dot blot are shown in FIG. 14. As can been seen in panels A and B, the translation products of both the Ψ and the U transcript give a signal when hybridized with the anti-His antibody. By contrast, only the translation product made from the Ψ transcript gives a signal with the anti-Flag antibody (compare panels C and D). These results strongly suggest that the translation machinery read through the ΨAA stop codon present in the Ψ transcript.

REFERENCES

Ast, G. (2004) How Did Alternative Splicing Evolve? Nat Rev Genet, 5: p.773-782.

Bachellerie, J. P., Michot, B., Nicoloso, M., Balakin, A., Ni, J., and Fournier, M. J. (1995) Antisense snoRNAs: a family of nucleolar RNAs with long complementarities to rRNA. Trends Biochem Sci, 20(7): p. 261-4.

Balakin, A. G., Smith, L., and Fournier, M. J. (1996) The RNA world of the nucleolus: two major families of small RNAs defined by different box elements with related functions. Cell, 86(5): p. 823-34.

Bertrand, E. and Bordonne, R. (2004) Assembly and traffic of small nuclear RNPs. Prog Mol Subcell Biol, 35: p. 79-97.

Bertrand, E., Houser-Scott, F., Kendall, A., Singer, R. H., and Engelke, D. R. (1998) Nucleolar localization of early tRNA processing Genes Dev, 12(16): p. 2463-8.

Burge, C. B., Tuschl, T., and Sharp, P. A. (1999) Splicing of precursors to mRNAs by the spliceosome, in *The RNA World*, R. F. Gesteland, T. R. Cech, and J. F. Atkins, Editors. Cold Spring Harbor Laboratory Press: Cold Spring Harbor. p. 525-560.

Cavaille, J., Buiting, K., Kiefmann, M., Lalande, M., Brannan, C. I., Horsthemke, B., Bachellerie, J. P., Brosius, J., and Huttenhofer, A. (2000) Identification of brain-specific and imprinted small nucleolar RNA genes exhibiting an unusual genomic organization. *Proc Natl Acad Sci USA*, 97(26): p. 14311-6.

Cavaille, J., Nicoloso, M., and Bachellerie, J. P. (1996) Targeted ribose methylation of RNA in vivo directed by tailored antisense RNA guides. *Nature*, 383(6602): p. 732-5.

Cortes, J. J., Sontheimer, E. J., Seiwert, S. D., and Steitz, J. A. (1993) Mutations in the conserved loop of human U5 snRNA generate use of novel cryptic 5' splice sites in vivo. *Embo J*, 12(13): p. 5181-9.

Frey, M. R. and Matera, A. G. (2001) RNA-mediated interaction of Cajal bodies and U2 snRNA genes. *J Cell Biol*, 154(3): p. 499-509.

Gall, J. G. (2001) A role for Cajal bodies in assembly of the nuclear transcription machinery. *FEBS Lett*, 498(2-3): p. 164-7.

Gall, J. G. (2003) The centennial of the Cajal body. *Nat Rev Mol Cell Biol*, 4(12): p. 975-80.

Ganot, P., Bortolin, M. L., and Kiss, T. (1997) Site-specific pseudouridine formation in preribosomal RNA is guided by small nucleolar RNAs. *Cell*, 89(5): p. 799-809.

Gerbi, S. A. and Lange, T. S. (2002) All small nuclear RNAs (snRNAs) of the [U4/U6.U5] Tri-snRNP localize to nucleoli; Identification of the nucleolar localization element of U6 snRNA. *Mol Biol Cell*, 13(9): p. 3123-37.

Hannon, G. J., Maroney, P. A., Denker, J. A. & Nilsen, T. W. Trans splicing of nematode pre-messenger RNA in vitro. *Cell* 61, 1247-55 (1990).

Jady, B. E. and Kiss, T. (2001) A small nucleolar guide RNA functions both in 2'-O-ribose methylation and pseudouridylation of the US spliceosomal RNA. *Embo J*, 20(3): p. 541-51.

Keller, E. B. and Noon, W. A. (1984) Intron splicing: a conserved internal signal in introns of animal pre-mRNAs. *Proc Natl Acad Sci USA*, 81(23): p. 7417-20.

Kiss, T. (2001) Small nucleolar RNA-guided post-transcriptional modification of cellular RNAs. *Embo J*, 20(14): p. 3617-22.

Kiss, T. (2002) Small nucleolar RNAs: an abundant group of noncoding RNAs with diverse cellular functions. *Cell*, 109 (2): p. 145-8.

Kiss-Laszlo, Z., Henry, Y., Bachellerie, J. P., Caizergues-Ferrer, M., and Kiss, T. (1996) Site-specific ribose methylation of preribosomal RNA: a novel function for small nucleolar RNAs. *Cell*, 85(7): p. 1077-88.

Lange, T. S. and Gerbi, S. A. (2000) Transient nucleolar localization Of U6 small nuclear RNA in *Xenopus* Laevis oocytes. *Mol Biol Cell*, 11(7): p. 2419-28.

Langford, C. J. and Gallwitz, D. (1983) Evidence for an intron-contained sequence required for the splicing of yeast RNA polymerase 11 transcripts. *Cell*, 33(2): p. 519-27.

Lerner, M. R., Boyle, J. A., Mount, S. M., Wolin, S. L., and Steitz, J. A. (1980) Are snRNPs involved in splicing? *Nature*, 283(5743): p. 220-4.

Liang, X. H., Xu, Y. X., and Michaeli, S. (2002) The spliced leader-associated RNA is a trypanosome-specific sn(o) RNA that has the potential to guide pseudouridine formation on the SL RNA. *Rna*, 8(2): p. 237-46.

Lowe, T. M., Eddy, S. R. (1999) A computational screen for methylation guide snoRNAs in yeast. *Science* 283:1168-1171.

Ma, X., Zhao, X., and Yu, Y. T. (2003) Pseudouridylation (Psi) of U2 snRNA in *S. cerevisiae* is catalyzed by an RNA-independent mechanism. *Embo J*, 22(8): p. 1889-97.

Maden, B. E., Corbett, M. E., Heeney, P. A., Pugh, K. & Ajuh, P. M. Classical and novel approaches to the detection and localization of the numerous modified nucleotides in eukaryotic ribosomal RNA. *Biochimie* 77, 22-9 (1995).

Massenet, S., Motorin, Y., Lafontaine, D. L., Hurt, E. C., Grosjean, H., and Branlant, C. (1999) Pseudouridine mapping in the *Saccharomyces cerevisiae* spliceosomal U small nuclear RNAs (snRNAs) reveals that pseudouridine synthase pus1p exhibits a dual substrate specificity for U2 snRNA and tRNA. *Mol Cell Biol*, 19(3): p. 2142-54.

Mattaj, I. W. (1988) U snRNP assembly and transport, in *Structure and function of major and minor small nuclear ribonucleoprotein particles*, B. M. L., Editor. Springer-Verlag Press: Heidelberg. p. 100-114.

Mount, S. M. (1982) A catalogue of splice junction sequences. *Nucleic Acids Res*, 10(2): p. 459-72.

Narayanan, A., Speckmann, W., Terns, R., and Terns, M. P. (1999) Role of the box C/D motif in localization of small nucleolar RNAs to coiled bodies and nucleoli. *Mol Biol Cell*, 10(7): p. 2131-47.

Newby, M. I. and Greenbaum, N. L. (2002) Sculpting of the spliceosomal branch site recognition motif by a conserved pseudouridine. *Nat Struct Biol*, 9(12): p. 958-65.

Newman, A. and Norman, C. (1991) Mutations in yeast U5 snRNA alter the specificity of 5'splice-site cleavage. *Cell*, 65(1): p. 115-23.

Newman, A. J. and Norman, C. (1992) U5 snRNA interacts with exon sequences at 5' and 3'splice sites. *Cell*, 68(4): p. 743-54.

Ni, J., Tien, A. L., and Fournier, M. J. (1997) Small nucleolar RNAs direct site-specific synthesis of pseudouridine in ribosomal RNA. *Cell*, 89(4): p. 565-73.

Parker, R., Siliciano, P. G., and Guthrie, C. (1987) Recognition of the TACTAAC box during mRNA splicing in yeast involves base pairing to the U2-like snRNA. *Cell*, 49(2): p. 229-39.

Peculis, B. (1997) RNA processing: pocket guides to ribosomal RNA. *Curr Biol*, 7(8): p. R480-2.

Phizicky E. M., Martzen M. R., McCraith S. M., Spinelli S. L., Xing F, Shull N. P., Van Slyke C, Montague R. K., Torres F. M., Fields S, Grayhack E. J (2002) Biochemical genomics approach to map activities to genes. *Methods Enzymol*, 350: p. 546-59.

Query, C. C., Moore, M. J., and Sharp, P. A. (1994) Branch nucleophile selection in pre-mRNA splicing: evidence for the bulged duplex model. *Genes Dev*, 8(5): p. 587-97.

Reed, R. and Maniatis, T. (1985) Intron sequences involved in lariat formation during pre-mRNA splicing. *Cell*, 41(1): p. 95-105.

Ruskin, B., Krainer, A. R., Maniatis, T., and Green, M. R. (1984) Excision of an intact intron as a novel lariat structure during pre-mRNA splicing in vitro. *Cell*, 38(1): p. 317-31.

Sleeman, J., Lyon, C. E., Platani, M., Kreivi, J. P., and Lamond, A. I. (1998) Dynamic interactions between splicing snRNPs, coiled bodies and nucleoli revealed using snRNP protein fusions to the green fluorescent protein *Exp Cell Res*, 243(2): p. 290-304.

Smith, C. M. and Steitz, J. A. (1997) Sno storm in the nucleolus: new roles for myriad small RNPs. *Cell*, 89(5): p. 669-72.

Smith, K. P. and Lawrence, J. B. (2000) Interactions of U2 gene loci and their nuclear transcripts with Cajal (coiled) bodies: evidence for PreU2 within Cajal bodies. *Mol Biol Cell*, 11(9): p. 2987-98.

Sontheimer, E. J. and Steitz, J. A. (1993) The U5 and U6 small nuclear RNAs as active site components of the spliceosome. *Science*, 262(5142): p. 1989-96.

Staley, J. P. and Guthrie, C. (1998) Mechanical devices of the spliceosome: motors, clocks, springs, and things. *Cell*, 92(3): p. 315-26.

Stanek, D. and Neugebauer, K. M. (2004) Detection of snRNP assembly intermediates in Cajal bodies by fluorescence resonance energy transfer. *J Cell Biol*, 166(7): p. 1015-25.

Steitz, J. A. and Tycowski, K. T. (1995) Small RNA chaperones for ribosome biogenesis. *Science*, 270(5242): p. 1626-7.

Thompson, M., Haeusler, R. A., Good, P. D., and Engelke, D. R. (2003) Nucleolar clustering of dispersed tRNA genes. *Science*, 302(5649): p. 1399-401.

Tycowski, K. T., Smith, C. M., Shu, M. D., and Steitz, J. A. (1996) A small nucleolar RNA requirement for site-specific ribose methylation of rRNA in *Xenopus*. *Proc Natl Acad Sci USA*, 93(25): p. 14480-5.

Valcarcel, J., Singh, R., Zamore, P. D., and Green, M. R. (1993) The protein Sex-lethal antagonizes the splicing factor U2AF to regulate alternative splicing of transformer pre-mRNA. *Nature*, 362(6416): p. 171-5.

Verheggen, C., Lafontaine, D. L., Samarsky, D., Mouaikel, J., Blanchard, J. M., Bordonne, R., and Bertrand, E. (2002) Mammalian and yeast U3 snoRNPs are matured in specific and related nuclear compartments. *Embo J*, 21(11): p. 2736-45.

Verheggen, C., Mouaikel, J., Thiry, M., Blanchard, J. M., Tollervey, D., Bordonne, R., Lafontaine, D. L., and Bertrand, E. (2001) Box C/D small nucleolar RNA trafficking involves small nucleolar RNP proteins, nucleolar factors and a novel nuclear domain. *Embo J*, 20(19): p. 5480-90.

Voet, D., Voet, J. G., *Biochemistry*, $2^{nd}$ Edition, John Wiley and Sons, Inc., New York, 1995.

Wu, J. and Manley, J. L. (1989) Mammalian pre-mRNA branch site selection by U2 snRNP involves base pairing *Genes Dev*, 3(10): p. 1553-61.

Wu, S., Romfo, C. M., Nilsen, T. W., and Green, M. R. (1999) Functional recognition of the 3' splice site AG by the splicing factor U2AF35. *Nature*, 402(6763): p. 832-5.

Wyatt, J. R., Sontheimer, E. J., and Steitz, J. A. (1992) Site-specific cross-linking of mammalian U5 snRNP to the 5' splice site before the first step of pre-mRNA splicing *Genes Dev*, 6(12B): p. 2542-53.

Yu, Y. T., Scharl, E. C., Smith, C. M., and Steitz, J. A. (1999) The growing world of small nuclear ribonucleoproteins, in *The RNA World*, R. F. Gesteland, T. R. Cech, and J. F. Atkins, Editors. Cold Spring Harbor Laboratory Press: Cold Spring Harbor. p. 487-524.

Yu, Y. T., Shu, M. D., and Steitz, J. A. (1998) Modifications of U2 snRNA are required for snRNP assembly and pre-mRNA splicing. *Embo J*, 17(19): p. 5783-95.

Yu, Y. T., Shu, M. D., Narayanan, A., Terns, R. M., Terns, M. P., and Steitz, J. A. (2001) Internal modification of U2 small nuclear (sn)RNA occurs in nucleoli of *Xenopus* oocytes. *J Cell Biol*, 152(6): p. 1279-88.

Yu, Y. T., Terns, R. M., and Terns, M. P. (2005) Mechanisms and functions of RNA-guided RNA modification, in *Topics in Current Genetics*, H. Grosjean, Editor. Springer-Verlag: New York. p. 223-262.

Zebarjadian, Y., King, T., Fournier, M. J., Clarke, L., and Carbon, J. (1999) Point mutations in yeast CBF5 can abolish in vivo pseudouridylation of rRNA. *Mol Cell Biol*, 19(11): p. 7461-72.

Zeitlin, S. and Efstratiadis, A. (1984) In vivo splicing products of the rabbit beta-globin pre-mRNA. *Cell*, 39(3 Pt 2): p. 589-602.

Zhao, X. and Yu, Y. T. (2004) Pseudouridines in and near the branch site recognition region of U2 snRNA are required for snRNP biogenesis and pre-mRNA splicing in *Xenopus* oocytes. *Rna*, 10(4): p. 681-90.

Zhao, X., Li, Z. H., Terns, R. M., Terns, M. P., and Yu, Y. T. (2002) An H/ACA guide RNA directs U2 pseudouridylation at two different sites in the branchpoint recognition region in *Xenopus* oocytes. *Rna*, 8(12): p. 1515-25.

Zhuang, Y. and Weiner, A. M. (1986) A compensatory base change in U1 snRNA suppresses a 5' splice site mutation. *Cell*, 46(6): p. 827-35.

Zhuang, Y. and Weiner, A. M. (1989) A compensatory base change in human U2 snRNA can suppress a branch site mutation. *Genes Dev*, 3(10): p. 1545-52.

What is claimed is:

1. A method for silencing a gene comprising: contacting a pre-mRNA transcript encoded by the gene with an engineered RNA; wherein the engineered RNA is a box C/D small nucleolar RNA able to cause a 2'-O-methylation modification of a branch point adenosine in the transcript and silence the gene.

2. The method of claim 1, wherein the modification prevents the branch point from initiating splicing of the transcript.

3. A method for silencing a gene in a mammal comprising, providing a cell with a DNA sequence encoding an engineered box C/D small nucleolar RNA able to cause a 2'-O-methylation modification of a branch point adenosine in a transcript encoded by the gene and silence the gene.

4. The method of claim 3, wherein the DNA sequence provided is a viral vector.

5. The method of claim 3, wherein the modification prevents the branch point from initiating pre-mRNA splicing.

6. The method of claim 3, wherein the gene is silenced to treat or prevent a disorder.

7. The method of claim 6, wherein the disorder to be treated or prevented is one or more of the group consisting of: a genetic disease a CNS disease; an inflammatory disease; a neurodegenerative disease; a cardiovascular disease; an autoimmune disease; and cancer.

8. The method of claim 7, wherein the genetic disease is one or more of the group consisting of: amyloidosis, LINCL, hemophilia, Alzheimer's disease, atherosclerosis, giantism, dwarfism, hypothyroidism, hyperthyroidism, cystic fibrosis, aging, obesity, Parkinson's disease, Niemann Pick's disease, cystic fibrosis, familial hypercholesterolemia, retinitis pigmentosa, Duchenne muscular dystrophy, and Marfan syndrome.

9. The method of claim 1, wherein the method is performed in vivo.

10. The method of claim 3, wherein the method is performed in vivo.

11. The method of claim 6, wherein the disorder to be treated or prevented is a genetic disease.

12. The method of claim 6, wherein the disorder to be treated or prevented is a CNS disease.

13. The method of claim 6, wherein the disorder to be treated or prevented is an inflammatory disease.

14. The method of claim 6, wherein the disorder to be treated or prevented is a neurodegenerative disease.

15. The method of claim 6, wherein the disorder to be treated or prevented is a cardiovascular disease.

16. The method of claim 6, wherein the disorder to be treated or prevented is an autoimmune disease.

17. The method of claim 6, wherein the disorder to be treated or prevented is cancer.

18. The method of claim 11, wherein the genetic disease is cystic fibrosis.

19. The method of claim 11, wherein the genetic disease is retinitis pigmentosa.

* * * * *

SEQUENCE LISTING

```
<160> NUMBER OF SEQ ID NOS: 7

<210> SEQ ID NO 1
<211> LENGTH: 3275
<212> TYPE: DNA
<213> ORGANISM: Artificial
<220> FEATURE:
<223> OTHER INFORMATION: plasmid sequence

<400> SEQUENCE: 1
ctaaattgta agcgttaata ttttgttaaa attcgcgtta aatttttgtt aaatcagctc      60
attttttaac caataggccg aaatcggcaa aatcccttat aaatcaaaag aatagaccga     120
gatagggttg agtgttgttc cagtttggaa caagagtcca ctattaaaga acgtggactc     180
caacgtcaaa gggcgaaaaa ccgtctatca gggcgatggc ccactacgtg aaccatcacc     240
ctaatcaagt tttttggggt cgaggtgccg taaagcacta aatcggaacc ctaaagggag     300
cccccgattt agagcttgac ggggaaagcc ggcgaacgtg gcgagaaagg aagggaagaa     360
```

```
agcgaaagga gcgggcgcta gggcgctggc aagtgtagcg gtcacgctgc gcgtaaccac      420
cacacccgcc gcgcttaatg cgccgctaca gggcgcgtcc cattcgccat tcaggctgcg      480
caactgttgg gaagggcgat cggtgcgggc ctcttcgcta ttacgccagc tggcgaaagg      540
gggatgtgct gcaaggcgat taagttgggt aacgccaggg ttttcccagt cacgacgttg      600
taaaacgacg gccagtgagc gcgcgtaata cgactcacta tagggcgaat tgggtaccgg      660
gccccccctc gagagctgat ccgttcgtcc tcactctctt ccgcatcgct gtctgcgagg      720
gccagctgtt ggggtgagta ctccctctca aaagcgggca tgacttctgc gctaagattg      780
tcagtttcca aaaacgagga ggatttgata ttcacctggc ccgcggtgat gcctttgagg      840
gtggccgcgt ccatctggtc agaaaagaca atcttttgt tgtcaagctt gacctgcacg       900
tctagggaat tccacgtgac cggtgatatc cgcggttgag gacaaactct tcgcggtctt      960
tccagtactc ttggatcgga aacccgtcgg cctccgaacg gtaagagcct agcatgtaga     1020
actggttgac ggggatccac tagttctaga gcggccgcca ccgcggtgga gctccagctt     1080
ttgttcccct tagtgagggt taattgcgcg cttggcgtaa tcatggtcat agctgtttcc     1140
tgtgtgaaat tgttatccgc tcacaattcc acacaacata cgagccggaa gcataaagtg     1200
taaagcctgg ggtgcctaat gagtgagcta actcacatta attgcgttgc gctcactgcc     1260 cgcttttccag tcgggaaacc tgtcgtgcca gctgcattaa tgaatcggcc aacgcgcggg    1320
gagaggcggt ttgcgtattg ggcgctcttc cgcttcctcg ctcactgact cgctgcgctc     1380
ggtcgttcgg ctgcggcgag cggtatcagc tcactcaaag gcggtaatac ggttatccac     1440 agaatcagg gataacgcag gaaagaacat gtgagcaaaa ggccagcaaa aggccaggaa      1500
ccgtaaaaag gccgcgttgc tggcgttttt ccataggctc cgcccccctg acgagcatca     1560 caaaatcga cgctcaagtc agaggtggcg aaacccgaca ggactataaa gataccaggc      1620
gtttccccct ggaagctccc tcgtgcgctc tcctgttccg accctgccgc ttaccggata     1680
cctgtccgcc tttctccctt cgggaagcgt ggcgctttct catagctcac gctgtaggta     1740
tctcagttcg gtgtaggtcg ttcgctccaa gctgggctgt gtgcacgaac cccccgttca     1800
gcccgaccgc tgcgccttat ccggtaacta tcgtcttgag tccaacccgg taagacacga     1860
cttatcgcca ctggcagcag ccactggtaa caggattagc agagcgaggt atgtaggcgg     1920
tgctacagag ttcttgaagt ggtggcctaa ctacggctac actagaagga cagtatttgg     1980
tatctgcgct ctgctgaagc cagttacctt cggaaaaaga gttggtagct cttgatccgg     2040
caaacaaacc accgctggta gcggtggttt ttttgtttgc aagcagcaga ttacgcgcag     2100
aaaaaaagga tctcaagaag atcctttgat cttttctacg gggtctgacg ctcagtggaa     2160
cgaaaactca cgttaaggga ttttggtcat gagattatca aaaaggatct tcacctagat     2220
ccttttaaat taaaaatgaa gttttaaatc aatctaaagt atatatgagt aaacttggtc     2280
tgacagttac caatgcttaa tcagtgaggc acctatctca gcgatctgtc tatttcgttc     2340
atccatagtt gcctgactcc ccgtcgtgta gataactacg atacgggagg gcttaccatc     2400
tggccccagt gctgcaatga taccgcgaga cccacgctca ccggctccag atttatcagc     2460
aataaaccag ccagccggaa gggccgagcg cagaagtggt cctgcaactt tatccgcctc     2520
catccagtct attaattgtt gccgggaagc tagagtaagt agttcgccag ttaatagttt     2580
gcgcaacgtt gttgccattg ctacaggcat cgtggtgtca cgctcgtcgt ttggtatggc     2640
ttcattcagc tccggttccc aacgatcaag gcgagttaca tgatccccca tgttgtgcaa     2700
aaaagcggtt agctccttcg gtcctccgat cgttgtcaga agtaagttgg ccgcagtgtt     2760
```

```
atcactcatg gttatggcag cactgcataa ttctcttact gtcatgccat ccgtaagatg    2820
cttttctgtg actggtgagt actcaaccaa gtcattctga aatagtgta tgcggcgacc    2880 gagttgctct tgcccggcgt caatacggga taataccgcg ccacatagca gaactttaaa    2940
agtgctcatc attggaaaac gttcttcggg gcgaaaactc tcaaggatct taccgctgtt    3000
gagatccagt tcgatgtaac ccactcgtgc acccaactga tcttcagcat cttttacttt    3060
caccagcgtt tctgggtgag caaaaacagg aaggcaaaat gccgcaaaaa agggaataag    3120
ggcgacacgg aaatgttgaa tactcatact cttccttttt caatattatt gaagcattta    3180
tcagggttat tgtctcatga gcggatacat atttgaatgt atttagaaaa ataaacaaat    3240 agggggttccg cgcacatttc cccgaaaagt gccac                              3275

<210> SEQ ID NO 2
<211> LENGTH: 11
<212> TYPE: RNA
<213> ORGANISM: Saccharomyces cerevisiae

<400> SEQUENCE: 2
aguuccacua c                                                          11

<210> SEQ ID NO 3
<211> LENGTH: 11
<212> TYPE: RNA
<213> ORGANISM: Saccharomyces cerevisiae

<400> SEQUENCE: 3
guaguagaac u                                                          11

<210> SEQ ID NO 4
<211> LENGTH: 20
<212> TYPE: RNA
<213> ORGANISM: Saccharomyces cerevisiae

<400> SEQUENCE: 4
uacuaacauc gauugcuuca                                                 20

<210> SEQ ID NO 5
<211> LENGTH: 19
<212> TYPE: RNA
<213> ORGANISM: Saccharomyce cerevisiae

<400> SEQUENCE: 5
ccaagcaauc gauguuagu                                                  19

<210> SEQ ID NO 6
<211> LENGTH: 19
<212> TYPE: RNA
<213> ORGANISM: Saccharomyces cervisiae

<400> SEQUENCE: 6
ccagcaaucg auguuagua                                                  19

<210> SEQ ID NO 7
<211> LENGTH: 19
<212> TYPE: RNA
<213> ORGANISM: Saccharomyces cerevisiae

<400> SEQUENCE: 7
ccugaagcaa ucgauguua                                                  19
```